(12) United States Patent
Strand et al.

(10) Patent No.: US 8,037,902 B2
(45) Date of Patent: *Oct. 18, 2011

(54) FLUID LOGIC DEVICE

(75) Inventors: David Strand, Sherborn, MA (US); Dan M. Leatzow, Kalispell, MT (US)

(73) Assignee: Protasis Corporation, Marlborough, MA (US)

( * ) Notice: Subject to any disclaimer, the term of this patent is extended or adjusted under 35 U.S.C. 154(b) by 1058 days.

This patent is subject to a terminal disclaimer.

(21) Appl. No.: 10/557,916

(22) PCT Filed: May 19, 2004

(86) PCT No.: PCT/US2004/016267
§ 371 (c)(1),
(2), (4) Date: Jan. 30, 2007

(87) PCT Pub. No.: WO2004/104555
PCT Pub. Date: Dec. 2, 2004

(65) Prior Publication Data
US 2007/0163663 A1    Jul. 19, 2007

Related U.S. Application Data

(60) Provisional application No. 60/471,617, filed on May 19, 2003.

(51) Int. Cl.
*G01N 27/00* (2006.01)

(52) U.S. Cl. .................................... 137/827; 204/601

(58) Field of Classification Search ............... 137/827; 204/450, 451, 454, 600, 601, 644, 548
See application file for complete search history.

(56) References Cited

U.S. PATENT DOCUMENTS

| 1,559,035 | A | * | 10/1925 | Gustav et al. ............... 204/563 |
| 4,112,743 | A | | 9/1978 | Mowery, Jr. et al. |
| 4,908,112 | A | | 3/1990 | Pace |
| 5,880,071 | A | | 3/1999 | Parce et al. |
| 6,277,258 | B1 | * | 8/2001 | Ivory et al. ................. 204/450 |
| 6,321,791 | B1 | | 11/2001 | Chow |
| 6,681,788 | B2 | | 1/2004 | Parce et al. |

FOREIGN PATENT DOCUMENTS

| WO | WO 02/28509 A2 | 4/2002 |
| WO | WO 02/28531 A1 | 4/2002 |
| WO | WO 02/28532 A2 | 4/2002 |
| WO | WO 02/44744 A1 | 6/2002 |
| WO | WO 02/056049 A2 | 7/2002 |

OTHER PUBLICATIONS

International Search Report for PCT/US04/16267, published May 12, 2005.

* cited by examiner

*Primary Examiner* — Craig Schneider
(74) *Attorney, Agent, or Firm* — Banner & Witcoff, Ltd.

(57) ABSTRACT

Novel fluid logic devices are disclosed. Certain examples of the fluid logic devices include two or more fluid logic gates that are each operative to select and/or direct analytes in a sample into one or more fluid flow channels in communication with the fluid logic gates. The fluid logic device can be part of a larger system, such as a chromatography system, or can be stand-alone device.

1 Claim, 34 Drawing Sheets

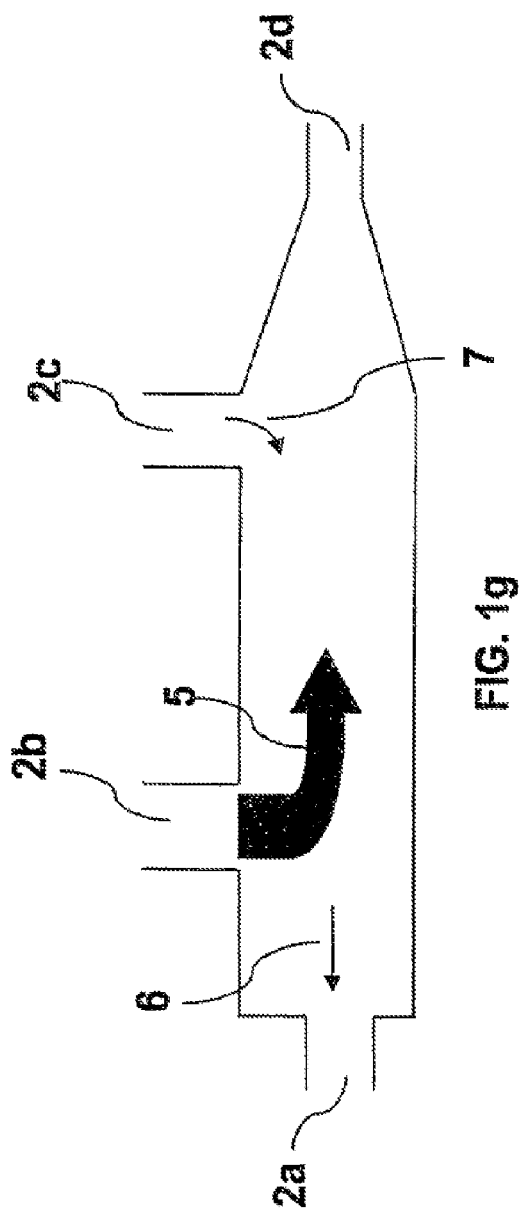
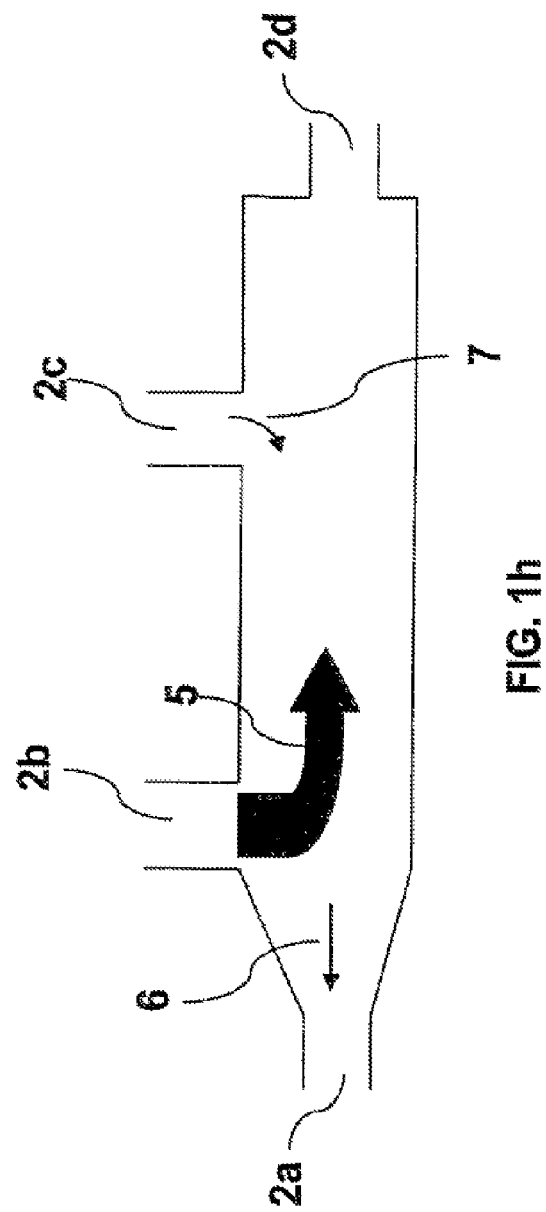

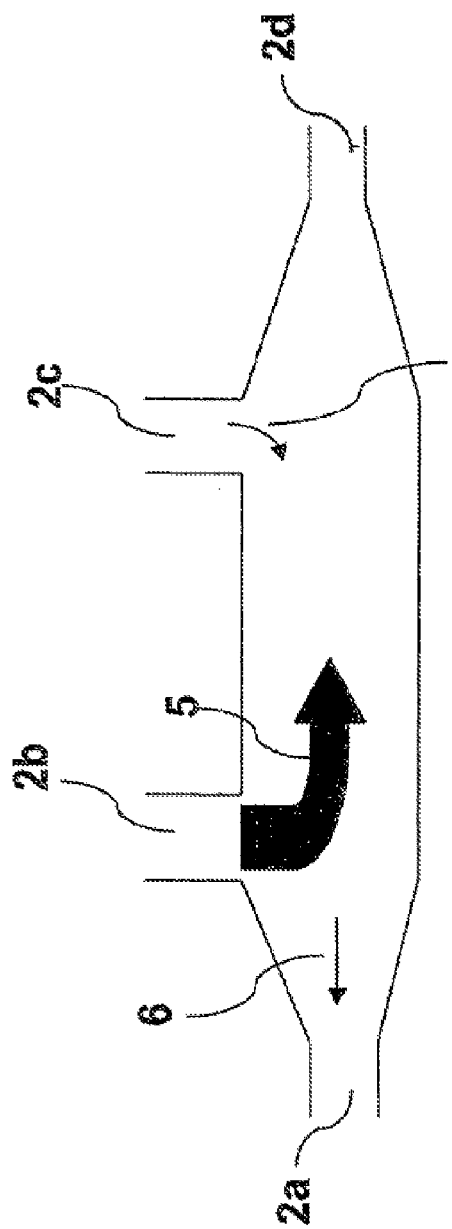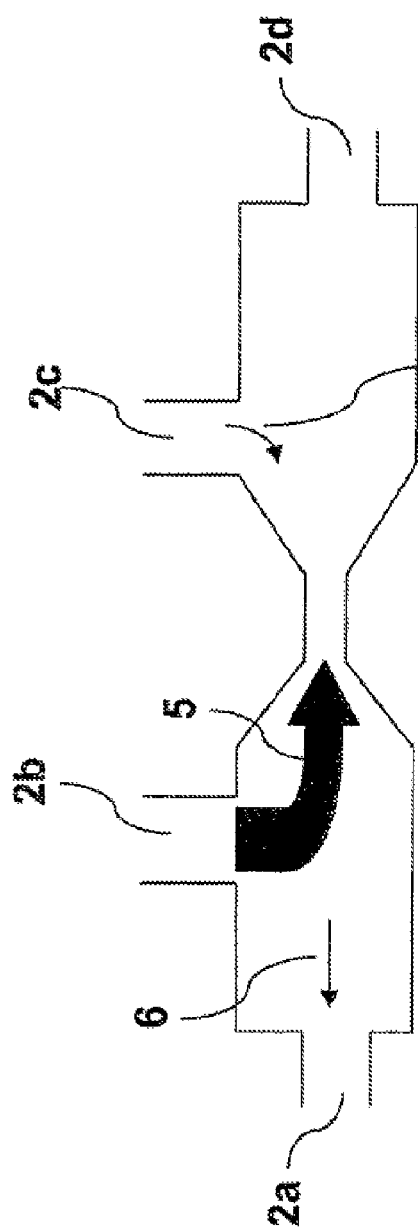
FIG. 1i
FIG. 1j

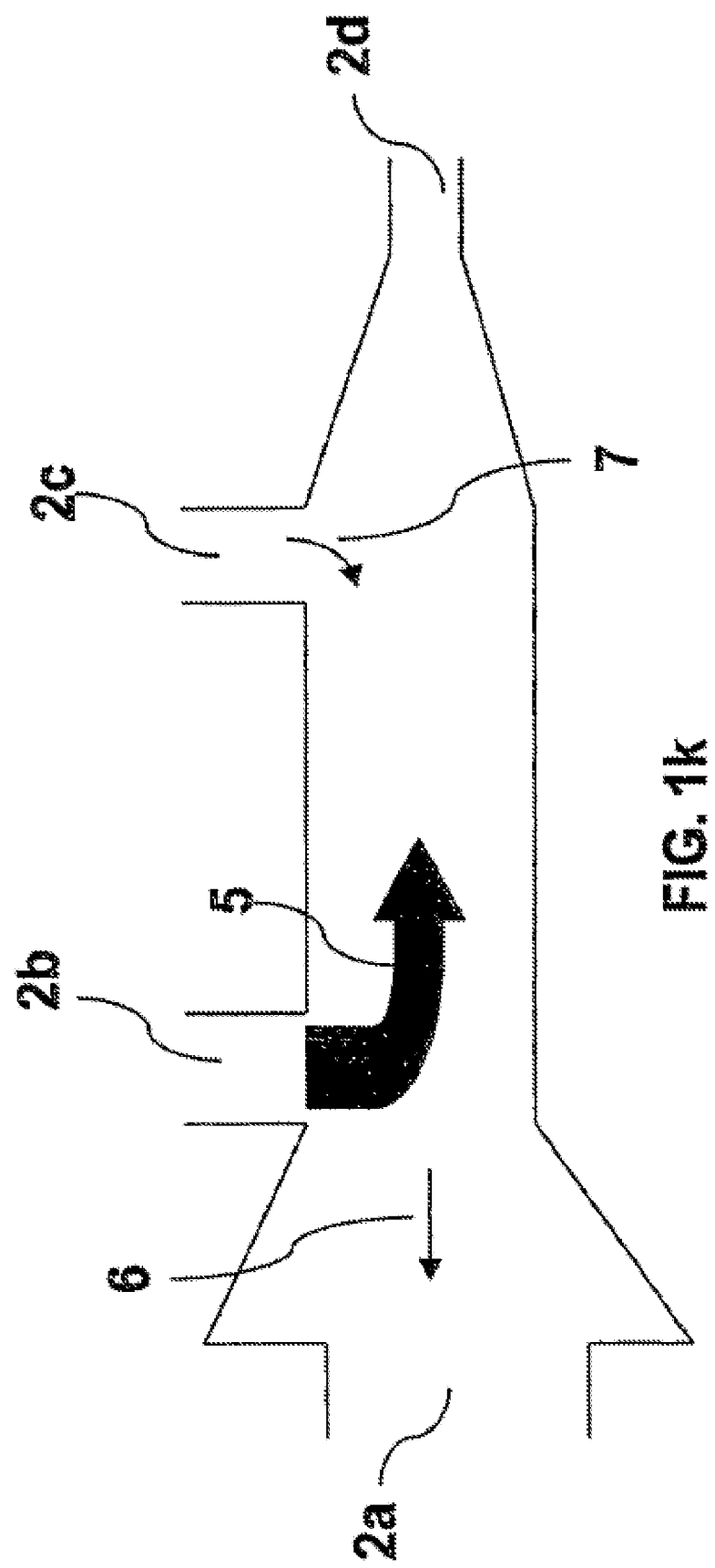

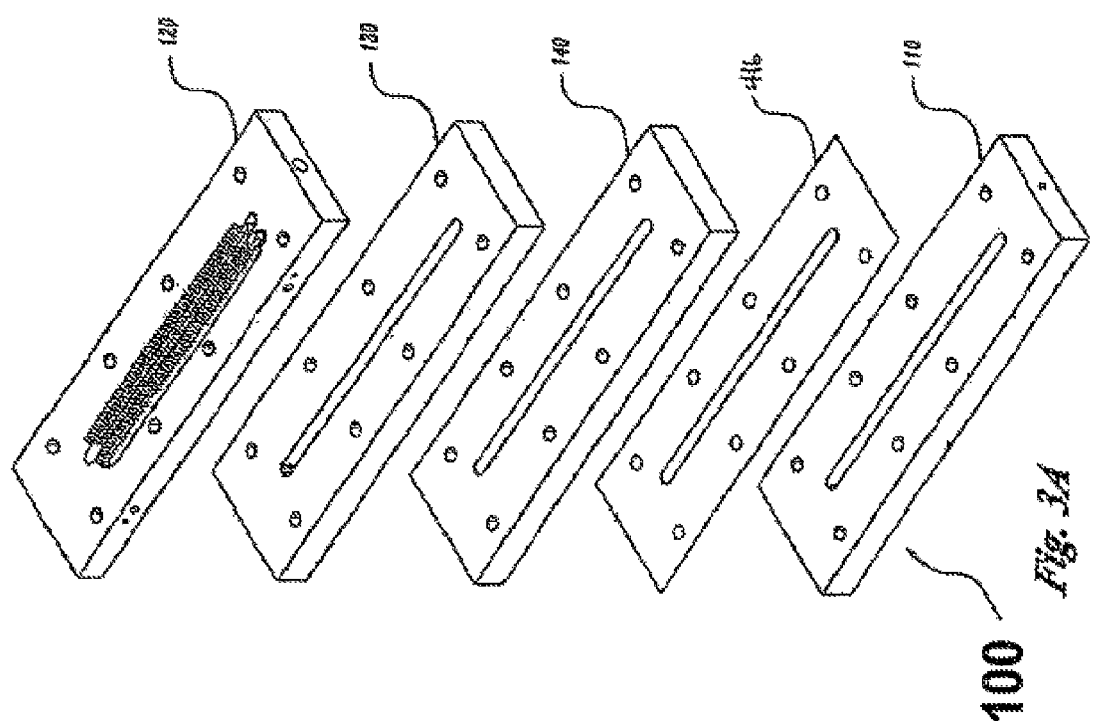

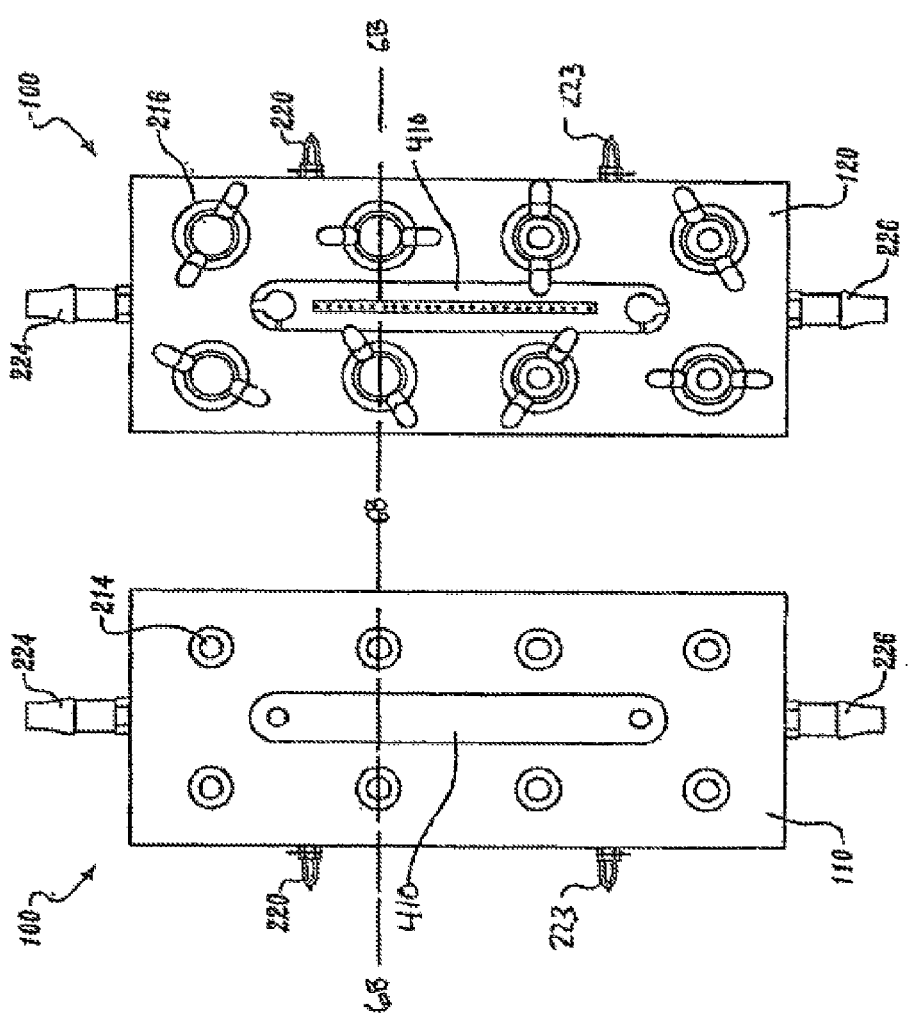

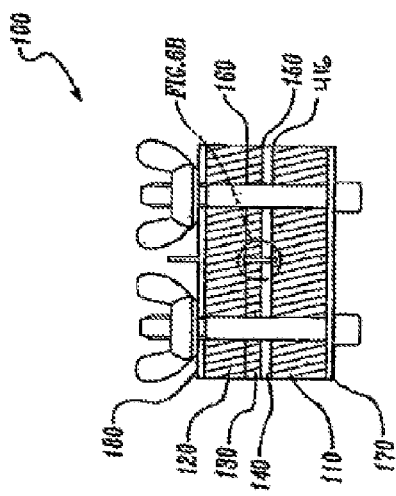
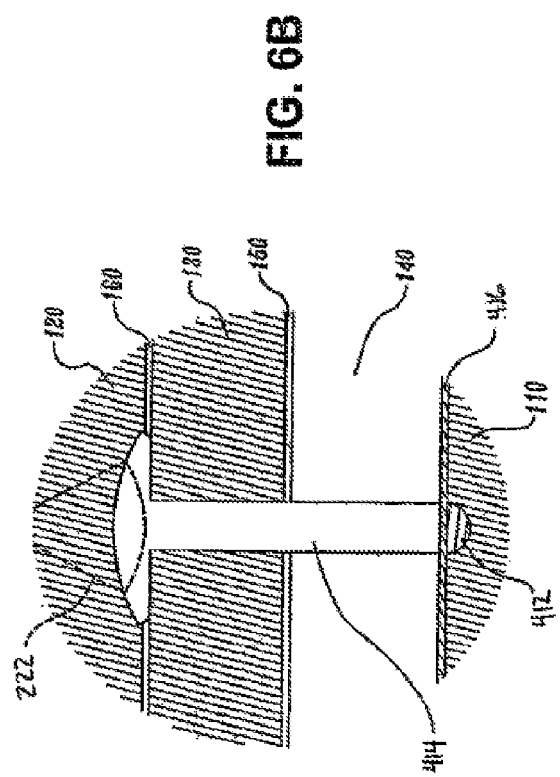

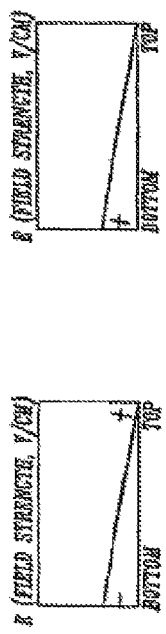
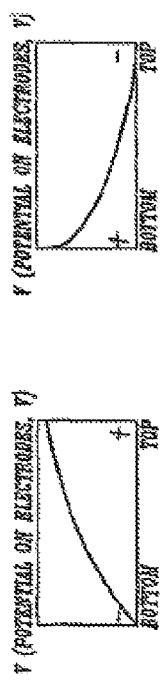
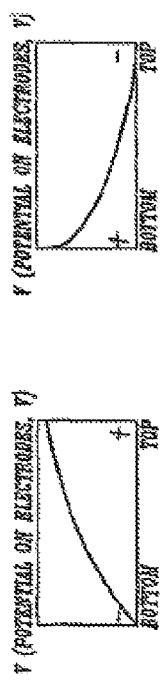
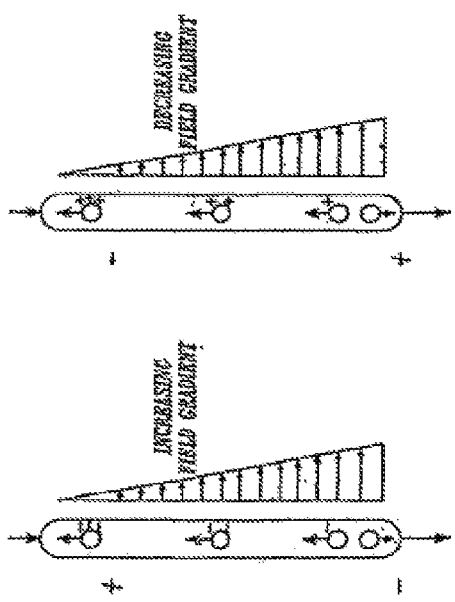
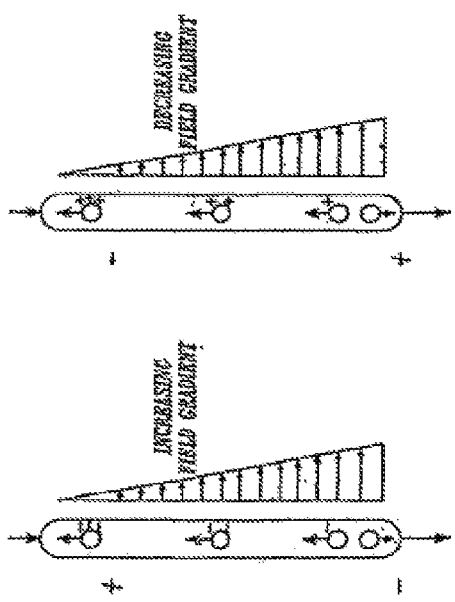

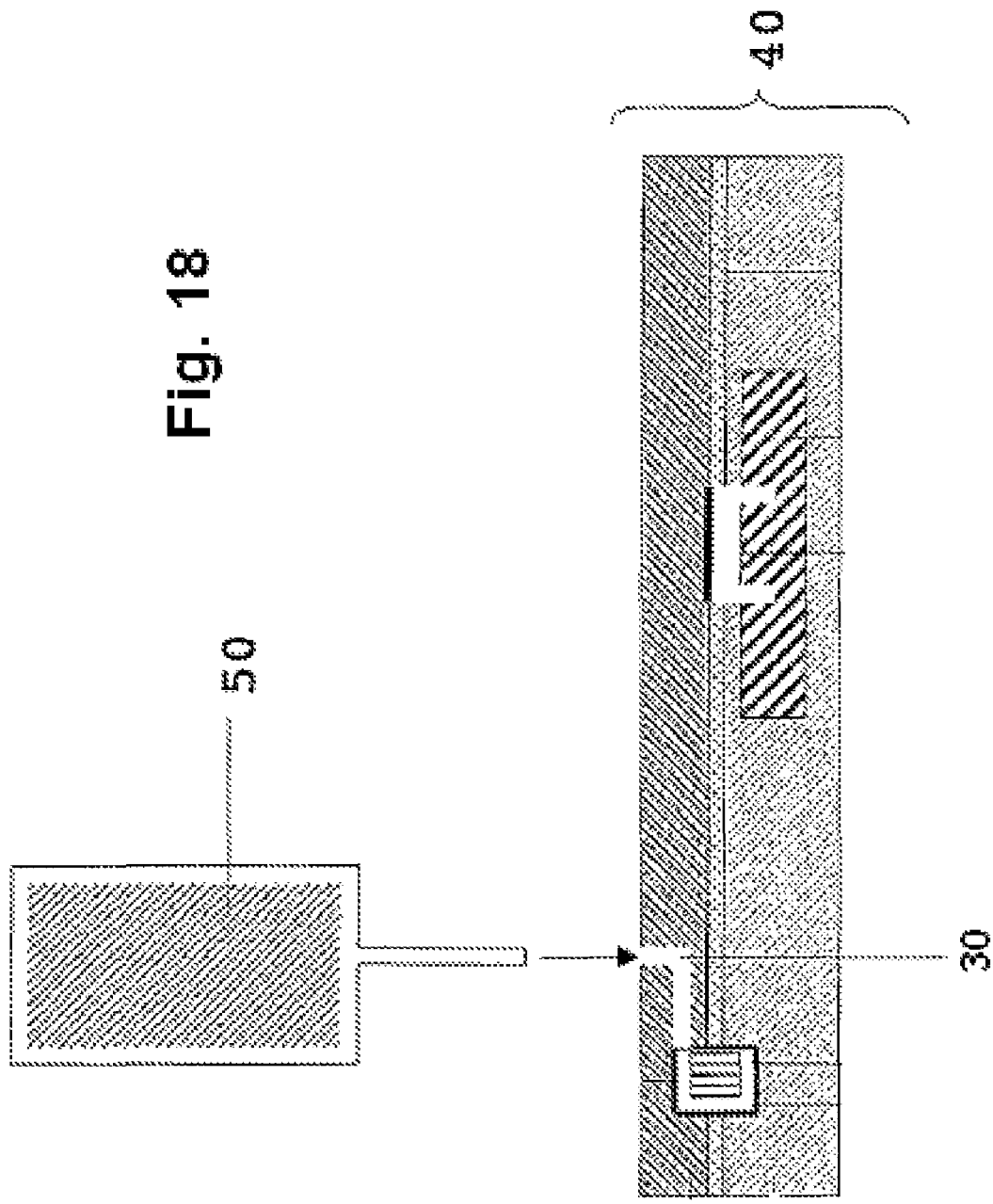

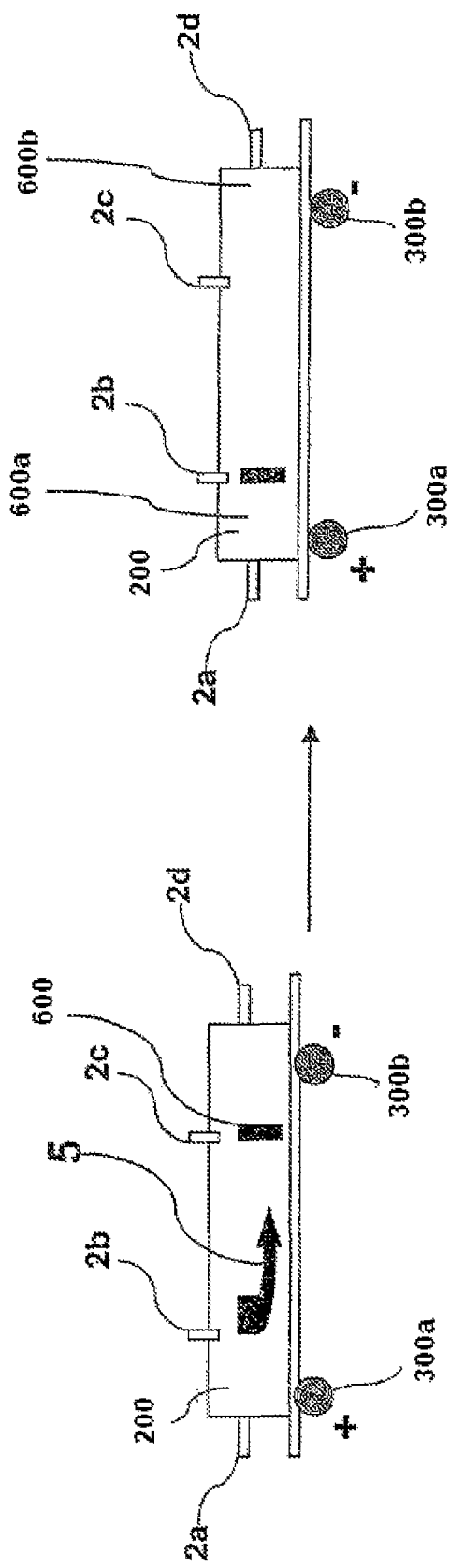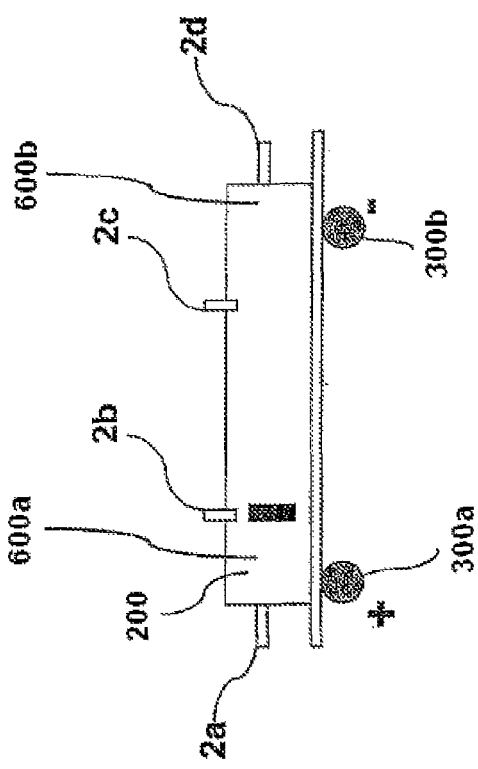
FIG. 19a
FIG. 19b
FIG. 19c

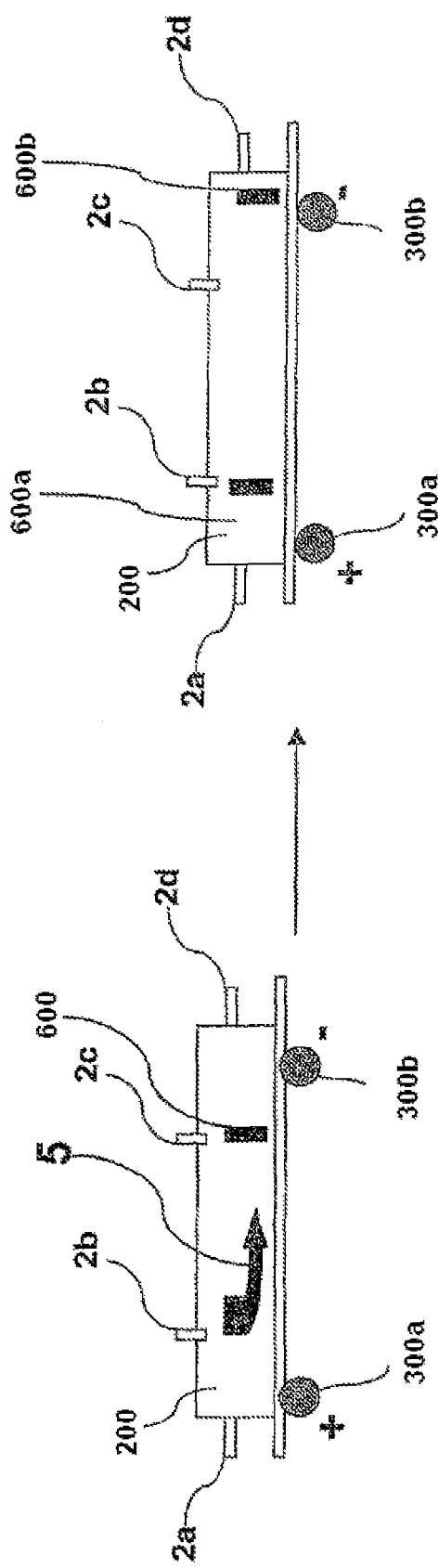

FLUID LOGIC DEVICE

PRIORITY CLAIM

This application is a 35 U.S.C. §371 National Phase filing of PCT Application No. PCT/US04/016267 filed 19 May 2004, which application claimed priority of the following commonly owned U.S. Provisional Patent Application Ser. No. 60/471,617, filed 19 May 2003. The PCT application designated the United States and was published in the English language on 2 Dec. 2004 as WO 04/104555 A2.

FIELD OF THE INVENTION

The present invention relates to fluid logic devices and more particularly to fluid logic devices comprising at least two fluid logic gates and to methods of making and using certain examples of such fluid logic devices.

CROSS-REFERENCED APPLICATIONS

The present application is directed to subject matter related at least in part to commonly assigned provisional patent applications U.S. Application Ser. No. 60/440,150, entitled "Devices and Methods for Focusing Analytes in an Electric Field Gradient," filed on 15 Jan. 2003; U.S. Application Ser. No. 60/440,105, entitled "Method and Apparatus for Determining the Isoelectric Point of a Charged Analyte," filed on 15 Jan. 2003; U.S. Application Ser. No. 60/430,943, entitled "Electrophoresis Device, System and Method for Sample Management and Hyphenation of Analytical Instruments," filed on Dec. 2, 2002; U.S. Application Ser. No. 60/447,997, entitled "Electrophoresis Device, System and Method for Sample Management and Hyphenation of Analytical Instruments," filed on Feb. 18, 2003; U.S. Application Ser. No. 60/471,616, entitled "Electrophoresis Device, System and Method for Sample Management and Hyphenation of Analytical Instruments," filed on May 19, 2003; U.S. Application Ser. No. 60/471,681, entitled "Method and Apparatus for Determining the Isoelectric Point of a Charged Analyte," filed on May 19, 2003; U.S. Application Ser. No. 60/471,597, entitled "Devices and Methods for Focusing Analytes in an Electric Field Gradient," filed on May 19, 2003; U.S. Application Ser. No. 60/471,623, entitled "Electrophoresis Devices and Methods for Focusing Charged Analytes," filed on May 19, 2003; U.S. Application Ser. No. 60/471,595, entitled "Electrophoresis Devices and Methods for Focusing Charged Analytes," filed on May 19, 2003, and commonly assigned published PCT applications WO 0228531 entitled "Fluid Separation Conduit Cartridge With Encryption Capability," WO 0228509 entitled "Fluid Separation Conduit Cartridge," WO 0228532 entitled "Microfluidic Substrate Assembly And Method For Making Same," WO 02056049 entitled "Microfluidic Device With Multiple Microcoil NMR Detectors," WO 0244744 entitled "Steep Solvent Gradient NMR Analysis Method," the entire disclosure of each of which his hereby incorporated by reference in its entirety for all purposes.

BACKGROUND

Systems for biochemical, chemical, and molecular analysis can be miniaturized as substrates with multifunctional capabilities including, for example, chemical, optical, fluidic, electronic, acoustic, and/or mechanical functionality. Miniaturization of these systems offers several advantages, including increased portability and lower production costs.

There exists a need in the art for fluid logic devices with separation and analytic capabilities, and for methods for manufacturing such devices. It is a general object of the present invention to provide fluid logic devices including at least two fluid logic gates and particularly micro-fluidic fluid logic devices comprising at least two fluid logic gates. These and other objects of the invention will be more fully understood from the following disclosure and detailed description of certain examples.

SUMMARY

In accordance with a first aspect, a fluid logic device is provided. The fluid logic device comprises a substrate comprising at least one flow channel and at least one inlet port. The fluid logic device further comprises at least two fluid logic gates. Each of the fluid logic gates is operative to perform one or more unit operations on fluid and/or analytes in the flow channel. Exemplary unit operations are discussed below. In certain examples, each fluid logic gate comprises a bulk fluid flow gate as described in the commonly assigned provisional application incorporated by reference. In other examples, the fluid logic gates function to direct an analyte into one or more flow channels. It will be recognized by the person of ordinary skill in the art, given the benefit of this disclosure, that the fluid logic gates of the fluid logic devices disclosed here need not perform the same function. That is, the function of one fluid logic gate may differ from the function of another fluid logic gate. The chamber optionally can be a packed chamber or unpacked. Any suitable packing can be used, of which many are commercially available and well known to those skilled in the art. The electric field can be a constant electric field, i.e., a uniform field, or a gradient electric field, i.e., a field whose strength varies along the chamber. In either case the electric field can be a static electric field during all or a selected period of processing, or a dynamic electric field, that is, a field whose shape is changeable with time use of the device.

In accordance with another aspect, each of the fluid logic gates of the fluid logic device provided here comprises a bulk fluid flow gate. That is, in certain examples, the fluid logic device comprises a first bulk fluid flow gate in fluid communication with a second bulk fluid flow gate. In at least certain examples, a bulk fluid flow gate is provided, that is operative to generate a hydrodynamic force and an opposed electric field in a flow cell, and is useful in analysis, testing and/or separation of one or more analytes. The bulk fluid flow gates comprises a first fluid flow chamber, and at least one electrode operative when energized to generate an electric field in the first fluid flow chamber. The first fluid flow chamber comprises a first fluid inlet port configured to receive bulk fluid flow into the first fluid flow chamber, a first fluid outlet port configured to pass bulk fluid from the first chamber, a second fluid inlet port configured to receive sample fluid flow into the first fluid flow chamber at a location between the first fluid inlet port and the first fluid outlet port, and a second fluid outlet port configured to pass fluid from the first fluid flow chamber. The first fluid outlet port and the second fluid outlet port are on opposite sides of the first fluid inlet port. The bulk fluid flow gate, when receiving a bulk fluid flow into the first fluid flow chamber via the first fluid inlet port and simultaneously a sample fluid flow into the first fluid flow chamber via the second inlet port, presents greater hydrodynamic resistance to passing fluid from the first fluid flow chamber via the second outlet port than via the first fluid outlet port. In some examples, a bulk fluid flow gate includes at least a first chamber that is configured to experience an electric field, as discussed in more detail below. The first chamber typically includes a plurality of ports. The first chamber includes a first entry port for introducing bulk fluid into the first chamber and a first exit port for exiting of bulk fluid from the first chamber. The first chamber also includes a second entry port positioned between the first entry port and the first exit port, i.e., the second entry port is positioned downstream of the first entry port. The second entry port is for introducing sample into the first chamber. As discussed in more detail below, the sample typically includes one or more analytes, e.g., charged and/or uncharged analytes. The first chamber further includes a second exit port which typically is positioned upstream of the first entry port. That is, the second exit port is typically positioned upstream from the point where bulk fluid is introduced into the first chamber so that the hydrodynamic resistance at the second exit port is substantially less than the hydrodynamic resistance at the first exit port.

In accordance with another aspect, each of the bulk fluid flow gates of the fluid logic devices experiences an electric field. In certain examples, a first electrode is in communication with the first bulk fluid flow gate and generates an electric field experienced by the first chamber of the first bulk fluid flow gate, and a second electrode is in communication with the second bulk fluid flow gate and generates an electric field experienced by the first chamber of the second bulk fluid flow gate. In other examples, the electric field may be generated using a pair of electrodes. In yet other examples, the electric field is generated using an electrode array. Numerous examples below discuss the use of a single electrode, pairs of electrodes and electrode arrays. In addition, the person of ordinary skill in the art, given the benefit of this disclosure, will readily be able to select other suitable methods and devices for generating an electric field that is experienced by the first chamber. The electric field is designed to provide a motive force such that at least some analytes of the sample migrate in a direction that is substantially opposite the direction of bulk fluid flow. In certain examples, the electric field strength is selected such that some of the analytes can migrate against bulk fluid flow and exit upstream of the first entry port of one or both of the bulk fluid flow gates. In some examples, when the electric field drives the analyte with a greater force than the hydrodynamic force, the analyte will migrate upstream towards the second exit port of the first chamber of one or more of the bulk fluid flow gates.

In accordance with another aspect, the first entry port of the first chamber of bulk fluid flow gates introduces bulk fluid flow into the first chamber. The bulk fluid flow generates a hydrodynamic force directed substantially towards the first exit port. The first exit port experiences substantially greater hydrodynamic resistance than the second exit port. In certain examples, the first entry port is configured at substantially a ninety-degree angle to the axial direction of the first chamber. In other examples, the first port is configured at an obtuse angle, i.e., greater than 90 degrees and less than 180 degrees, to the axial direction of the first chamber. In yet other examples, the first port is moveable from an angle of about 90 degrees to an obtuse angle. Such movements typically are controlled electronically by a microprocessor or the like. One skilled in the art, given the benefit of this disclosure, will be able to select suitable first entry port angles depending on an intended use of the bulk fluid flow gate.

In accordance with other aspects, the second entry port of the first chamber of the bulk fluid flow gates introduces sample into the first chamber. The sample typically includes one or more analytes dissolved in a suitable solvent. The composition of the solvent may be the same or different from the composition of bulk fluid introduced through the first entry port. The samples can be introduced through the second entry port using numerous methods and devices including syringes, pumps, injectors and the like. In certain examples, the sample is introduced using an auto-injector. The person of ordinary skill in the art, given the benefit of this disclosure, will be able to select suitable devices and methods for introducing samples into the first chamber of the devices disclosed here.

In accordance with another aspect, the first exit port of the bulk fluid flow gates is positioned downstream from the first entry port and downstream from the second entry port. As bulk fluid is introduced from the first entry port, the bulk fluid flows into the first chamber at a suitable velocity and volume such that greater hydrodynamic resistance exists at the first exit port than at the second exit port. A result of this greater hydrodynamic resistance is that an analyte proximate to the first exit port experiences great resistance to migration away from the first exit port. That is, the hydrodynamic force makes it difficult for the analyte to migrate upstream towards the second exit port. In certain examples it may be necessary to increase the electric field strength, decrease the hydrodynamic resistance, or both, such that the analyte can migrate towards the second exit port. The person of ordinary skill in the art, given the benefit of this disclosure, will be able to select suitable hydrodynamic resistances and electric field strengths.

In accordance with yet other aspects, the second exit port of the bulk fluid flow gates provided here is located upstream from the first entry port, the second entry port and the first exit port. A result of such location is that the second exit port experiences substantially lower hydrodynamic resistance than that experienced at the first exit port. Analytes that are positioned between the first entry port and the second exit port experience little hydrodynamic resistance and can exit the first chamber rapidly. Such decrease in hydrodynamic resistance may be linear, exponential, logarithmic or the like, and depends at least in part on the parameters selected, e.g., bulk flow velocity, electric field strength, etc., and the selected dimensions and shape of the first chamber. As discussed in more detail below, in examples where an analyte has migrated from the second entry port to the first entry port, the hydrodynamic resistance experienced by the analyte drops significantly once the analyte clears the first entry port.

In accordance with other aspects, the ports of the first chamber of the bulk fluid flow gates may be configured in numerous orientations with respect to the first chamber. In certain examples as discussed above, the first entry port and the second entry port each is configured at about a ninety-degree angle to the axial direction of the first chamber. In certain examples, the first entry port is configured at an obtuse angle, i.e., greater than ninety degrees and less than 180 degrees, to the axial direction of the first chamber. In certain examples, each of the first and second exit ports is parallel to the axial direction of the first chamber. As discussed below, other orientations are possible and will be recognized by the person of ordinary skill in the art given the benefit of this disclosure.

In accordance with certain aspects, the electric field is generated by at least one electrode. The electrode provides a driving force such that charged analytes migrate away from or towards the electrode. The electrode can be positively or negatively charged, but typically the electrode comprises a charge suitable to drive the analyte away from the electrode. In examples where the analyte is positively charged, the electrode is also positively charged to repel the analyte and drive the analyte away from the electrode. Without wishing to be bound by any particular scientific theory, it may be necessary or desirable to include a second electrode so that the bulk fluid flow gate operates for an intended purpose.

In accordance with other aspects, a pair of electrodes is used to generate an electric field, where one electrode of the electrode pair is typically positioned at one end of a bulk fluid flow gate and the second electrode of the electrode pair is typically positioned at an opposite end of a bulk fluid flow gate. Typically, one electrode of the electrode pair is positively charged and the other electrode of the electrode pair is negatively charged. Charged analyte introduced into the first chamber through the second entry port typically will migrate towards the electrode bearing an opposite charge to that of the analyte. However, as discussed further below, in certain examples the charge of one or more analytes may be altered or masked such that migration occurs in a direction that is substantially opposite the native charge of the analyte. It will be within the ability of the person of ordinary skill in the art, given the benefit of this disclosure, to select suitable operating conditions to achieve a desired result.

In accordance with other aspects, the electric field generated by the electrode(s) of the bulk fluid flow gate may be a constant or linear electric field or may be an electric field gradient of any suitable strength and shape, e.g., parabolic, segmented (i.e., having two or more segments each with a different slope), etc. In accordance with other aspects, the electrode chamber of the devices disclosed here comprises an electrode array. The electrode array comprises more than two electrodes, for example, 3 or more electrodes, e.g., about 3 to 50 electrodes or more. The electrodes, typically are arranged uniformly or non-uniformly along the axial length of the first chamber, e.g., the electrodes of the array may be spaced evenly throughout the electrode chamber or can have any suitable spacing selected by a user. It will be within the ability of those skilled in the art, given the benefit of this disclosure, to select a suitable number and spacing of electrodes, chamber shape (for both the separation chamber and the electrode chamber) to achieve the desired electric field shape and strength and the desired degree of control of electric field shape and strength. The electrodes can be microfabricated electrodes, e.g., microfabricated bio-electrodes. The electrodes can be protected electrodes, requiring no membrane between the separation chamber and the electrode chamber or simply positioned in the separation chamber. Each such electrode generally has a protective coating or membrane exclusionary of the target analyte and sufficiently permeable to electric current to establish the desired electric field in the separation chamber, optionally a porous membrane, e.g., an ion-exchange membrane. A via or porous material can be used to release gasses evolved at the electrode during operation. Each electrode is optionally capable of being individually controlled, i.e., energized at a level selected independently of the energization level of other electrodes in the array. In certain aspects, the electrode array is independently operative to generate an electric field gradient profile, that is to say, the electrode array can create a gradient in the electric field, the shape and/or strength of which is then acted upon by the non-uniformity of the separation chamber, the electrode(s), or both. In certain examples, the electrode array is operative to generate an electric field gradient profile in the first chamber that can be dynamically controlled. In other examples, the voltages of the electrodes of the electrode array typically are individually monitored and controlled to influence the shape and/or strength of the electric field gradient, with or without adjustment or change during the focusing process. Optionally, for example, the voltage applied to each electrode is controlled by a computer-controlled circuit board or suitable processor or the like in operative connection to a suitable voltage source. In certain examples, the electrode array is used to dynamically control the electric field gradient during migration of one or more analytes, for example, to shift the location of a stationary focused band within the first chamber to bring the band over an optional sampling port located on the first chamber from which the band(s) can be selectively removed.

In accordance with certain aspects, the first chamber of each of the bulk fluid flow gates can be designed to be uniform or non-uniform. A first chamber that is uniform typically has a substantially constant cross-sectional area in the axial direction. A first chamber that is non-uniform typically has a variable cross-sectional area in the axial direction. Similarly, each of the ports of the first chamber may be uniform or non-uniform. Uniform ports typically have a substantially constant cross-sectional area in the axial direction. Non-uniform ports typically have a variable cross-sectional area in the axial direction. In certain examples, a bulk fluid flow gate may include a uniform first chamber and uniform ports. In other examples, a bulk fluid flow gate may include a non-uniform first chamber and one or more uniform ports. In yet other examples, a bulk fluid flow gate may include a uniform first chamber and one or more non-uniform ports. In yet further examples, a bulk fluid flow gate may include a non-uniform chamber and one or more non-uniform ports. Depending on the intended use of the bulk fluid flow gate, the person of ordinary skill in the art, given the benefit of this disclosure, will be able to select and design bulk fluid flow gates including uniform first chambers, non-uniform first chambers and uniform and/or non-uniform ports.

In certain examples, the first chamber of each bulk fluid flow gate is a separation chamber designed to facilitate separation of analytes in a sample. As discussed in more detail below, the first chamber may include one or more separation media, e.g., chromatography media including but not limited to molecular sieves, ion-exchange media, size exclusion media, etc., for separation of the analytes in the sample.

In accordance with another aspect, the fluid logic devices disclosed here can be used in a wide range of automated tests for the analysis of a fluid. Testing or analysis of a fluid has a broad meaning, including any detection, measurement or other determination of the presence of a fluid or of a characteristic or property of the fluid or of a component of the fluid, such as particles, dissolved salts or other solutes or other species in the fluid. In yet other examples, the fluid logic device disclosed here is operative to perform liquid or gas separation analysis. That is, the devices perform or are adapted to function in a larger system that performs, any of various different liquid or gas separation tests or analysis methods, typically along with ancillary and supporting operations and equipment.

In accordance with a method aspect, the fluid logic devices disclosed selectively direct analytes into one or more fluid flow channels. In certain examples, sample is injected into the fluid logic device and enters into the first fluid logic gate. The first fluid logic gate is operative to select the direction that analytes of the sample migrate. Depending on the chosen hydrodynamic force and electric field strength, some analytes will migrate upstream towards the second exit port of the first fluid logic gate, whereas other analytes will migrate with bulk fluid flow towards first exit port of the first fluid logic gate. Another fluid logic gate may be in fluid communication with the second exit port of the first fluid logic gate. In addition, another fluid logic gate can be in fluid communication with the first exit port of the first fluid logic gate. The additional fluid logic gates function similar to the first fluid logic gate, i.e., are operative to perform unit operation on the sample to selectively control migration of the analytes in the sample. Depending on the operating conditions selected for each fluid logic gate, an analyte can be directed to any fluid flow channel desired by a user. It will be within the ability of the person of ordinary skill in the art, given the benefit of this disclosure, to use the fluid logic devices disclosed here for selectively directing one or more analytes of a sample.

In accordance with an additional method aspect, the fluid logic gate is operative to separate analytes in a fluid and then direct the analytes into a selected flow channel. In certain examples, the fluid logic gates separate the analytes through the use of bulk fluid and an electric field. In other examples, the fluid logic gate separates the analytes through the use of bulk fluid, the electric field and separation media contained with the first chamber of the fluid logic gate. The electric field drives migration of the analyte, whereas the bulk fluid typically flows against the direction of analyte migration to retard analyte migration. Without wishing to be bound by any particular scientific theory, at points where the hydrodynamic force and the force provided by the electric field substantially cancel each other, no net migration of the analyte will occur. That is, at points where they hydrodynamic force and the electric force are approximately the same, there is no net migration of the analyte in the fluid logic devices provided here.

In accordance with other aspects, the fluid logic devices disclosed here are "microfluidic" in that they operate effectively on micro-scale fluid samples, typically having fluid flow rates as low as about 1 mL/min, preferably 100 uL/min or less, more preferably 10 uL/min or less, most preferably 1 uL/min or less, for example 100 nanoliters/min. Total fluid volume for an LC or other such fluid separation performed by the fluid logic devices disclosed here, e.g., in support of a water quality test to determine the concentration of analytes in the water being tested, in accordance with certain preferred embodiments, can be as small as about 10 mL or less, or 1 mL or less, preferably 100 microliters, more preferably 10 microliters or even 1 microliter or less, for example, about 100 nanoliters. As used herein, the term "microscale" also refers to flow passages or channels and other structural elements of the fluid logic devices. For example, one or more flow channels of the substrate preferably have a cross-sectional dimension (diameter, width or height) between 500 microns and 100 nanometers. Thus, at the small end of that range, the microchannel has cross-sectional area of about 0.01 square microns. Such microchannels within the laminated substrate, and chambers and other structures within the laminated substrate, when viewed in cross-section, may be triangular, ellipsoidal, square, rectangular, circular or any other shape. It should be recognized, that one or more aspects of the fluid logic devices may in certain examples have operative features, such as fluid channels, reaction chambers or zones, accumulation sites, etc., that are larger than microscale. The fluid logic devices disclosed here provide effective fluid analysis systems with good speed of analysis, decreased sample and solvent consumption, the possibility of increased detection efficiency, and in certain examples disposable fluid logic devices.

In accordance with other aspects, the microfluidic nature of the fluid logic devices disclosed here provides significant commercial advantage. Less sample fluid is required, which in certain applications can present significant cost reductions, both in reducing product usage (for example, if the test sample is taken from a product stream) and in reducing the waste stream disposal volume. In addition, the fluid logic devices can, in accordance with preferred embodiments, be produced employing MEMS and other known techniques suitable for cost effective manufacture of miniature high precision devices. The micro-scale fluid flow channel(s) of the fluid logic devices and other operational features and components of the fluid logic devices, such as the fluid logic gate components for liquid chromatography or other fluid separation methods, heating or cooling fluid handled by the assembly, generating electrical or electromagnetic or acoustical (e.g., ultrasonic) forces on the fluid, generating high pressures or pressure differentials, fluid mixing, reacting, analyzing, extraction, amplification or focusing or concentration, labeling, filtering, selection, purification, etc. can be integrated into the fluid flow channel(s) of the fluid logic devices, can be mounted onto the fluid logic device as an on-board component or incorporated elsewhere in the fluid logic device. Such operational devices, including devices integrated as an external component-on-board mounted in fluid-tight fashion to the surface of the fluid logic device and/or devices embedded within the body of the fluid logic device, in accordance with certain examples of the fluid logic devices disclosed here, are micro-scale devices, as defined above.

In accordance with other aspects, fluid logic devices in accordance with the present disclosure incorporate multiple fluid flow gates, including, e.g., one or more of the above described fluid flow gates together, optionally, with one or more other types of fluid flow gates and/or other features, components, etc. In certain exemplary embodiments the fluid flow gates are arranged in series, such that an inlet port of a downstream fluid flow gate receives fluid flow from the exit port of an upstream fluid flow gate. In certain exemplary embodiments fluid flow gates are arranged in parallel, such that an inlet port of 2 or more downstream fluid flow gates each is in positioned to receive fluid flow simultaneously from a common upstream source. In certain exemplary embodiments fluid flow gates are arranged in any suitable combination or permutation of series and parallel fluid communication. It should be understood that, as used here and in the appended claims, unless clear otherwise from the context of a particular usage, words such as "a" and "an" and "the" etc. are used in accordance with convention and tradition to mean at least one. Likewise, a device or system of the like that "comprises" a certain feature or element can have one or more than one such feature or element and can also have any other elements or features, etc. Likewise, a device or system comprising two of something can have two or more than two of that thing, a device or system comprising three can have three or more than three, etc.

It will be recognized that the fluid logic devices disclosed here represent a significant technological advance. Robust fluid logic devices can be designed to perform separations, testing or other analyses on fluid comprising one or more analytes. It will be within the ability of the person of ordinary skill in the art, given the benefit of this disclosure to design fluid logic devices suitable for an intended use.

BRIEF DESCRIPTION OF THE DRAWINGS

Examples of the fluid logic devices disclosed here are discussed below with reference to the accompanying drawings in which:

FIGS. 1e-1l are cross-sectional views of bulk fluid flow gates for use in the fluid logic devices provided here;

FIG. 3A is an exploded view of another example of a bulk fluid flow gate of the fluid logic devices disclosed here;

FIGS. 5A and 5B are front and back plan views, respectively, of the device of FIGS. 3A-3E and 4, in assembly;

FIGS. 6A and 6B are views, partially in section, of the device of FIGS. 3A-3E, 4 and 5A-5B, in assembly, taken through line 6A-6A in FIG. 4 and line 6B-6B in FIGS. 5A and 5B, respectively;

FIGS. 7A-7F present schematic representations and graphical representations of two approaches for conducting electric field gradient focusing in FIG. 8 is a schematic drawing of another example of a device in accordance with the present disclosure;

FIG. 18 is a schematic illustration of a representative fluid-handling substrate with an external component.

FIGS. 19a-19c show use of the bulk fluid flow gate for an exemplary separation.

FIGS. 20a-20b show use of the bulk fluid flow gate for another exemplary separation.

Figure 1A:
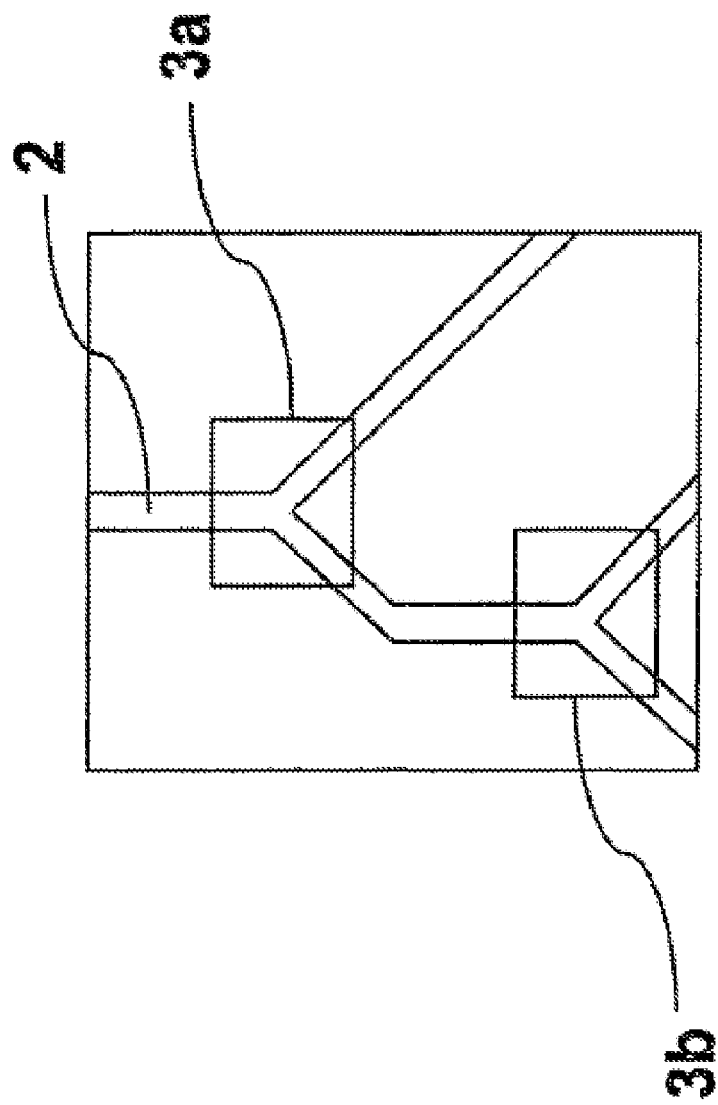
FIG. 1a is a cross-sectional view of a first example of a fluid logic device.

The dimensions, sizes, shapes and configurations of the figures are only representative of exemplary devices disclosed here. Other suitable dimensions, sizes, shapes and configurations will be readily selected by the person of ordinary skill in the art, given the benefit of this disclosure.

DETAILED DESCRIPTION OF CERTAIN EXAMPLES

Numerous examples and embodiments of the present invention are possible and will be apparent to the person of ordinary skill in the art, given the benefit of this disclosure. This detailed description of certain examples, for convenience only, will focus on certain illustrative examples generally used for separation, testing and analysis of one or more analytes in a sample. However, it will be within the ability of the person of ordinary skill in the art, given the benefit of the present disclosure, to use the fluid logic devices disclosed here for these and other uses.

Unless otherwise indicated or unless otherwise clear from the context in which it is described, the elements or features disclosed in the examples below and in the examples discussed in the Summary should be understood to be interchangeable with each other. That is, one or more elements described in one example may be interchanged or substituted for one or more elements described in another example. The elements of the examples should be understood to be disclosed generally for use with other aspects and examples of the devices and methods disclosed herein.

a. Multi-Laminate Fluid Logic Devices

The fluid logic devices disclosed here typically include a multi-laminate structure, such as the multi-laminate structures described in the commonly assigned published PCT applications incorporated by reference above. Reference should be made to those published PCT applications for a fuller discussion of such multi-laminate structures, but a brief discussion of multi-laminate fluid logic devices is presented below.

In certain examples, fluid logic devices comprise a multi-layer laminated substrate defining at least one fluid inlet port, at least one microscale fluid flow channel within the multi-layer substrate in fluid communication with the inlet port for transport of fluid to be tested and in fluid communication with at least one of the fluid logic gates of the fluid logic device. In certain examples, the microscale fluid flow channel is in communication with a plurality of fluid logic gates. In some examples, at least one operative component is mounted aboard the multi-layer laminated substrate in communication with the microscale fluid flow channel. In certain preferred embodiments the mounted component (referred to here also as a "component-on-board" or by similar term) is in fluid communication with the microchannel in the substrate. The component-on-board can be any of numerous components. Exemplary components include heaters, coolers, pumps, fluid reservoirs, etc. As discussed further below, any necessary or desired function not performed by a suitable component-on-board can be performed by other equipment associated with the fluid logic device. As an example of components of the fluid logic devices disclosed here, or the fluid logic devices incorporating or integrating such fluid logic devices, in certain examples will advantageously comprise a heating/cooling element for controlling the temperature of fluid being tested or measured and/or for heating/cooling the fluid logic gates. An electrical heating or cooling element may be integrated into the fluid logic devices. A microprocessor may be used to regulate the heating/cooling element and/or control other functions of the fluid logic devices. A thermocouple may also be provided in the fluid logic device in electrical contact with the associated device to allow such microprocessor or other electronic controller to detect and maintain desired fluid temperatures. A cooling element, such as a miniature thermoelectric heat pump (Materials Electronic Products Corp., Trenton, N.J.), may also be included in the associated device for adjusting the temperature of the fluid logic device and the fluid flow channels and fluids contained therein. It will be within the ability of the person of ordinary skill in the art, given the benefit of this disclosure, to select suitable heating and cooling elements for incorporation into the fluid logic devices disclosed here.

In accordance with certain examples, fluid logic devices are provided comprising a generally planar multi-layer laminated substrate defining at least one fluid inlet port, at least one microscale fluid flow channel at each of more than one level within the fluid logic device for transport of fluid to be tested, at least two fluid logic gates, and at least one microchannel extending between levels and/or between the fluid logic gates. In some examples, the microscale fluid flow channels at each of multiple levels within the device are formed at the surface-to-surface interfaces between layers of the substrate. Two levels of microchannels are formed, for example, by a polyetheretherketone (PEEK) or other plastic plate or disk having micromachined grooves on both an upper and lower surface and sandwiched between two other layers of the device. A through-hole micromachined or otherwise formed in the plastic plate passing from an upper surface groove to a lower surface groove provides a fluid communication via. In certain preferred embodiments one or both of the sandwiching layers of the device is a flexible sheet or film. As used here, the term "generally planar multi-layer laminated substrate" means card or cartridge-like, optionally being curvo-planar or otherwise irregular, but typically being rectilinear or right-cylindrical, and having a thickness less than about one third, preferably less than one quarter, more preferably less than about one fifth, e.g., about one sixth or less, the largest dimension of the major (i.e., largest) surface of the laminated substrate. The dimensions of the laminated substrate referred to here are measured without including any external components mounted on-board the substrate. Nor do they include electrical leads or conduits carrying sample fluid to or from the laminated substrate. One or both of the sandwiching layers can be welded or otherwise bonded, selectively or not, to the micromachined layer to provide fluid-tight sealing along the microchannels. Additional levels of microchannels are provided by stacking additional micromachined plates in the substrate. Directional references used here are for convenience only and not intended to limit the orientation in which the multi-layer laminated substrates are used. In general, the multi-layer laminated substrates can be used in any orientation; solely for purposes of discussion here, they are assumed to be in the orientation shown in the drawings appended hereto. Those skilled in the art will recognize, given the benefit of this disclosure, that microchannels and vias of the multi-layer laminated substrate can have any suitable configuration including straight, curvo-linear, serpentine or spiral. The cross-sectional configuration of the microchannels can be regular, i.e., uniform, or irregular, to suit the needs of an intended application.

In accordance with some examples, fluid logic devices are provided comprising a multi-layer laminated substrate defining at least one fluid inlet port, at least two fluid logic gates and at least one microscale fluid flow channel within the multi-layer substrate in fluid communication with the inlet port for transport of fluid to be tested, wherein at least one layer of the multi-layer laminated substrate is formed of plastic and the substrate assembly is operative and fluid tight at high fluid pressure in the microscale fluid flow channel. Certain examples are fluid tight and operative at fluid pressures in excess of 100 psig, preferably in excess of 200 psig, more preferably in excess of 300 psig, most preferably at pressures greater than 500 psig. Other examples are operative, including being fluid-tight along the periphery of the microchannels within the substrate, even at fluid pressure in the microscale fluid flow channel in excess of 1000 psig. Examples employing plastic substrate layers in high pressure examples provide significant advantages in manufacturing cost and flexibility. In accordance with some examples, the microfluidic substrate assembly employs a multi-layer laminated substrate having rigid plates sandwiching plastic layer between them. The plastic layers optionally are welded one to another and the rigid plates sandwiching the multiple plastic layer between them are formed of metal and are fastened directly to each other. As used here, direct fastening means that a bolt or other fastener has compressive contact with the rigid sandwiching plates. In some examples, multiple bolts or the like extend from one to the other of the rigid sandwiching plates. In accordance with other examples, grooves for fluid flow channels can be micromachined, laser cut or otherwise milled or formed in the inside surface of one or both metal (or other rigid material) clamping plates that may be, e.g., $3/16$ to 3 inch thick. When the substrate is assembled, a layer of PEEK or other plastic, e.g., 0.003-0.005 inch thick clamped between the plates, in cooperation with the clamping plates grooves, defines fluid-tight microchannels of the resulting fluid logic device. Through holes in the PEEK layer can serve as vertical channels in the substrate to provide fluid communication from microchannels in the inside surface of the top clamping plate to those in the lower clamping plate. It will be within the ability of the person of ordinary skill in the art, given the benefit of this disclosure, to design suitable multi-laminate fluid logic devices.

Other components may be includes in the multi-laminate fluid logic devices disclosed here. Such components include but are not limited to electronic memory components mounted to the substrate assembly and operatively connected to the another component of the microfluidic substrate assembly. Suitable I/O devices for uploading signals to the memory component or downloading information stored on it will be apparent to those skilled in the art given the benefit of this disclosure, and include, for example, PCMCIA-type electronic communication ports.

In certain examples, as discussed above, the fluid logic devices have a substrate assembly comprising a multi-layer laminated substrate microfabricated to define at least one microscale fluid flow passage. Numerous materials are suitable for the individual layers of the substrate, depending on the use environment and functionality intended for the device. Suitable materials include, for example, plastic, rigid or flexible, glass, ceramic, metal, silicon, etc. A layer formed of materials suitable for micromachining may be used, for example, with another layer formed of material compatible with waveguide, thick film, thin film or other surface treatments. Given the benefit of this disclosure, it will be within the ability of those skilled in the art to select materials for the substrate suited to the particular application. The substrate assembly may take any of numerous forms, e.g., a cartridge or a component of a cartridge for performing one or more operations on a fluid, for example, fluid analysis, testing, detection or the like, such as by liquid chromatography, gas chromatography, electrophoresis, or other liquid and gas separation and analytical techniques. As further discussed below, any one or more of various different operations may be performed by the substrate assembly, employing, for example, heating, cooling, electrical, magnetic, electromagnetic or acoustical (e.g., ultrasonic) forces, pressure differentials, etc. Exemplary unit operations which may be performed by various different embodiments of the substrate assembly disclosed here include fluid mixing, reacting, analyzing, extraction, amplification or focusing or concentration, labeling, filtering, selection, purification, etc. Information such as the identity of the substrate assembly, the results of any such operation(s) and/or when they occurred or the conditions at that time may optionally be digitally or otherwise recorded, such as in an on-board memory chip or the like carried by the substrate assembly or by another component of a system in which the substrate assembly is employed. One or more of the aforesaid operations may be integrated into the substrate assemblies disclosed herein.

In accordance with certain examples, fluid logic devices are provided having selectively welded joint or interfacial areas between adjacent layers, and having sealed channels incorporating environmentally sensitive elements, such as components embedded or housed within the channels or architectural micro-features. Exemplary embodiments include fluid logic devices incorporating architectural microstructures or housing fluid analysis, testing or flow-control components which are not tolerant of the temperatures at which the adjacent layers or components used to assemble the substrate would thermally weld together to from the fluid-tight microchannels. The elements are "not tolerant" in this context, in that the function or structure of the environmentally sensitive structure or element in question would be destroyed, impaired or undesirably altered by a thermal welding process in which substrate components are heated in bulk to the welding temperature.

In accordance with other examples, methods are provided for sealing together components, e.g., plastic layers, to form the fluid logic devices without the need for adhesives, solvents, or exposure of environmentally sensitive elements of the substrate to the high temperatures, intense radiation, or pressures typically employed when thermally welding plastic assemblies. In some examples, a method is provided for producing the fluid logic devices, comprising assemblies with internal fluid-tight sealed channels having environmentally sensitive elements and at least one fluid logic gate. Such method comprises assembling together components with an environmentally sensitive element and/or fluid logic gates incorporated in an internal channel, e.g., embedded or formed therein. The substrate components are then selectively welded together, preferably using IR radiation, to establish a fluid-tight seal along the periphery of the internal channel. Selective IR welding offers protection to the environmentally sensitive components because the components are not heated in bulk to the welding temperature, thus any environmentally sensitive element incorporated therein are not heated to such temperature. In some examples, the bulk material of the components adjacent to the location of the selective IR welding is selected for its ability to act as a heat sink, thereby providing thermal protection to an environmentally sensitive element near the site of the selective welding. Thus, the method in accordance with this example enables the sealing of channels, such as micro-channels in fluid logic devices, without destroying the environmentally sensitive elements and fluid logic gates contained in the channels. The fluid logic devices, in which environmentally sensitive elements and fluid logic gates can be incorporated without thermal damage, are especially advantageous in enabling fluid-handling substrates to be produced for use in a wide variety of applications including, for example, liquid chromatography and other fluid analysis, chemical and biochemical testing, detection and sensing and detection processes (in some cases referred to collectively below as fluid testing or as fluid analysis). It is also an advantage of at least certain examples, that fluid-tight sealing of the channels is accomplished without use of solvent or adhesive joining, thereby avoiding the problematic aspects of those methods discussed above.

In accordance with other examples, fluid logic devices are provided having selectively welded joint or interfacial areas between the device and an external component mounted to the substrate with a fluid-tight seal at a port in a surface of the device. Such external component (referred to in some instances below as a component-on-board), as disclosed above, can advantageously provide any of numerous functionalities to the fluid logic device. For illustrative purposes only, FIG. 18 shows an embodiment of a fluid-handling substrate containing an attached external component. An external component 50 is attached to a port 30 on the surface of the substrate 40. A component-on-board can act as a fluid reservoir, a mixer, a detector, an analyzer or serve other roles. The component-on-board may be permanently attached to the fluid logic device or may be a removable component-on-board, which is referred to in some instances below as a swappable component-on-board. A swappable component-on-board provides increased functionality to the fluid logic devices disclosed here. For example, the swappable component-on-board might be an apparatus for introducing a fluid, e.g., bulk fluid or fluid containing sample, into the fluid logic device. After introduction of the fluid, the swappable component-on-board might be replaced with a detector for analyzing the introduced fluid. The ability of a fluid logic device to interface with multiple different types of external components expands the potential application where a fluid logic device may be employed.

In accordance with other examples, fluid-tight seal between the component-on-board and the fluid logic devices may be accomplished using suitable devices and methods, such as those described in the commonly assigned published PCT applications incorporated by reference above. In addition, other suitable methods and devices will be readily apparent to the person of ordinary skill in the art, given the benefit of this disclosure.

Figure 1B:
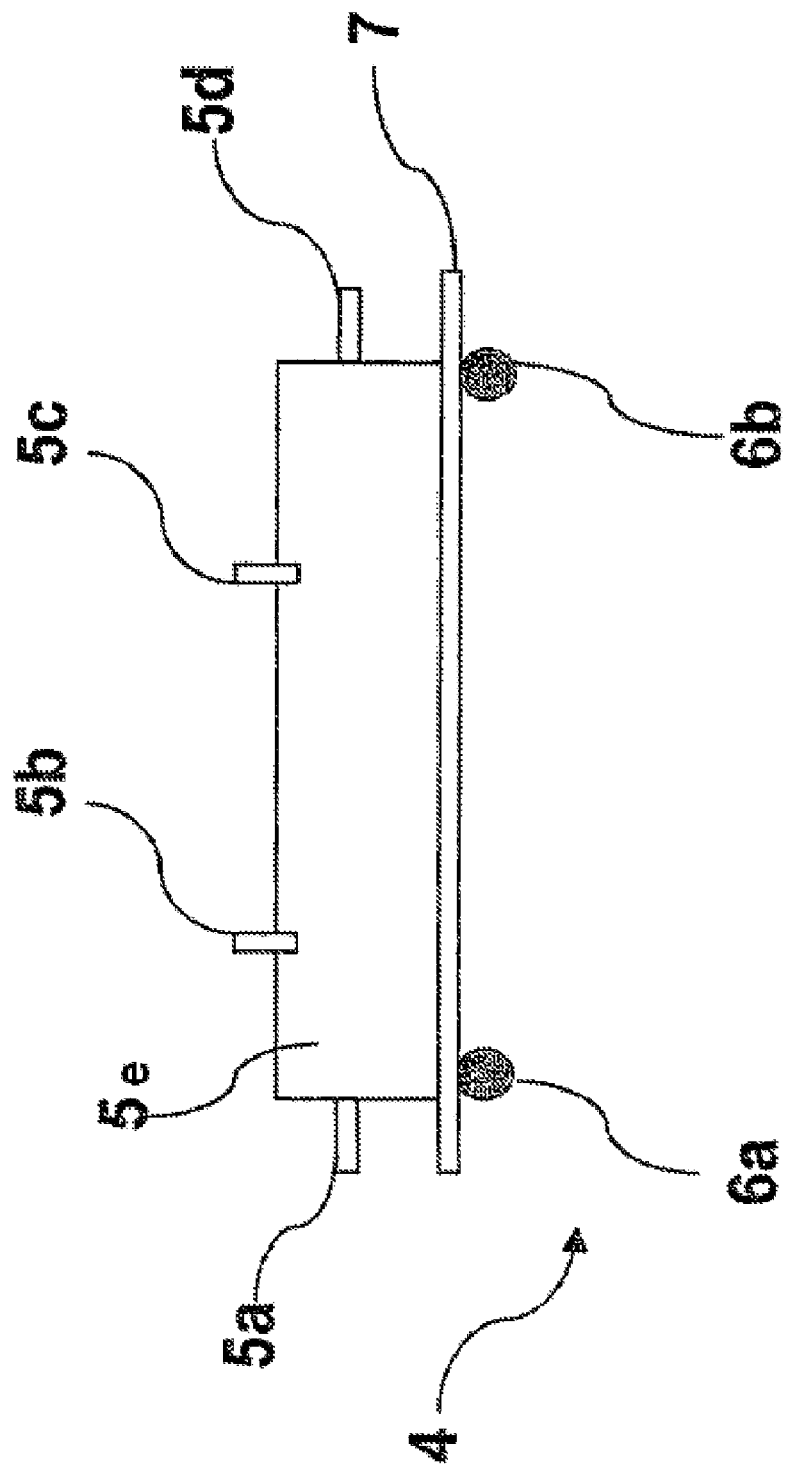
FIGS. 1b and 1c are cross-sectional views of other examples of fluid logic devices.

In accordance with certain examples and referring to FIG. 1a, a fluid logic device is provided comprising a first fluid flow channel 2, a first fluid logic gate 3a in fluid communication with the first fluid flow channel 2 and a second fluid logic gate 3b in fluid communication with the first fluid logic gate 3a. In this example, each of the fluid logic gates comprises a bulk fluid flow gate as discussed further below. In FIG. 1a, fluid flow channel 2 preferably is in fluid communication with the second entry port of the first fluid flow bulk gate. A cross-sectional view of a bulk fluid flow gate is shown in FIG. 1b. As discussed in more detail below, the second entry port of the fluid flow gates is for introducing sample into the bulk fluid flow gate. In certain examples, a bulk fluid flow gate 4 (see FIG. 1b) includes a first chamber 5e and a pair of electrodes 6a and 6b. The first chamber 5e includes first entry port 5b, second entry port 5c, first exit port 5d and second exit port 5a. Second entry port 5c is typically positioned between first entry port 5b and first exit port 5d. The bulk fluid flow gate typically also includes a first permeable material 7 that separates the first chamber 5e and electrodes 6a and 6b, which are operative to generate an electric field which is experienced by the first chamber and which drives migration of analytes introduced into the first chamber. First chamber 5e is in electrical communication and mass or ionic communication with electrodes 6a and 6b through permeable material 7. "Electrical communication" or "the electric field being experienced by the first chamber" refers to the ability of the electric field that is generated by the electrode(s) to be transferred, or to have an effect, within the first chamber, and may be by any means which accomplishes this result. The permeable material retains analytes in the first chamber and is permeable to certain analytes such that the electrodes and first chamber are in communication as noted above.

In certain examples, bulk fluid 5 is introduced into the fluid logic device and enters first chamber 5e through first entry port 5b (see FIG. 1b). Such bulk fluid may be introduced through a component on board, for example, or through a flow channel in fluid communication with first entry port 5b. Introduction of bulk fluid results in substantially greater hydrodynamic resistance downstream of first entry port 5b such that the hydrodynamic resistance at first exit port 5d is greater than the hydrodynamic resistance at second exit port 5a. Fluid flow which is upstream or first entry port 5b typically is of a lower volume and/or velocity than bulk fluid flow such that the hydrodynamic resistance at second exit port 5a is substantially less than the hydrodynamic resistance at first exit port 5d. As discussed above, sample is introduced into first chamber 5e through second entry port 5c. In the device shown in FIGS. 1a and 1b and in the presence of an electric field, charged analytes in the sample migrate either towards first exit port 5d or second exit port 5a. Charged analyte that is migrating towards first exit port 5d is aided in migration by bulk fluid flow. Charged analyte that is migrating towards second exit port 5a is retarded in migration by bulk fluid flow because bulk fluid flows in a substantially opposing direction to analytes migrating towards second exit port 5a. That is, bulk fluid flow acts to retard migration of sample towards second exit port 5a, and during migration of analyte in the first chamber, once the analyte migrates upstream of first entry port 5b, the retarding force exerted on the analyte by the bulk fluid flow is substantially reduced. Fluid upstream of first entry port 5a flows in a substantially opposite direction to that of bulk fluid. Bulk fluid flow acts as a gate to retard migration of sample introduced downstream of first entry port 5b, and once analyte migrates upstream of first entry port 5b, i.e., upstream of the gate, the hydrodynamic force and the migration force are substantially in the same direction.

Figure 1C:
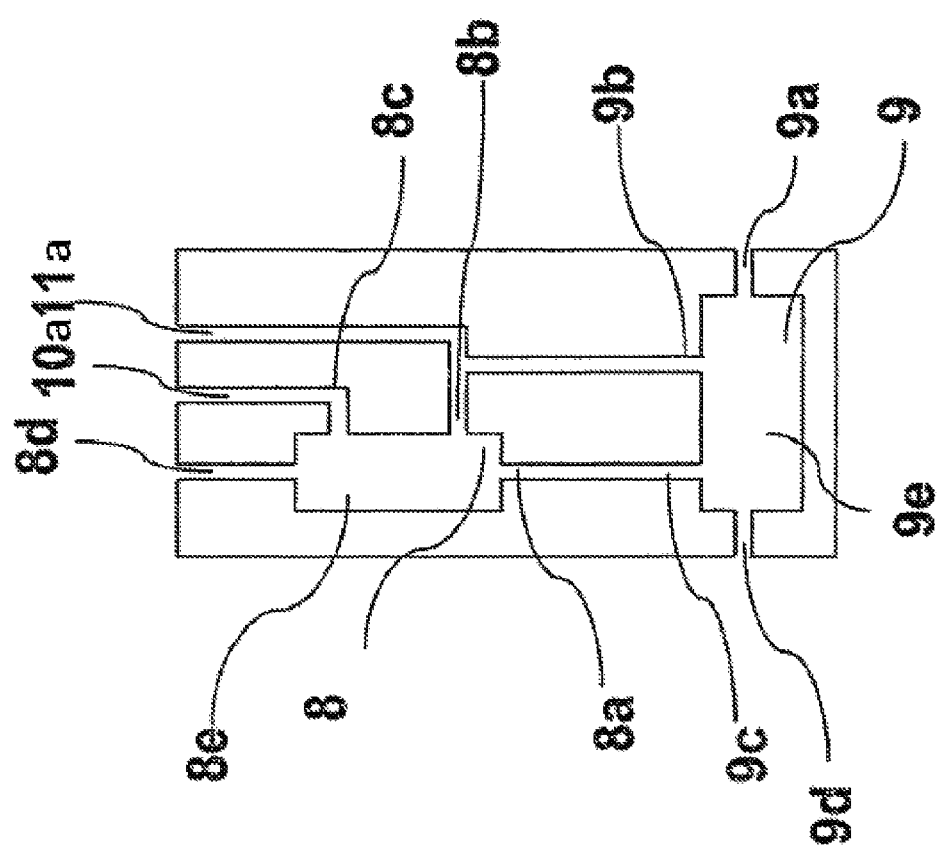

In FIG. 1c, an example of a fluid logic device is disclosed. The fluid logic device shown in FIG. 1c includes a first bulk fluid flow gate 8 in fluid communication with a second bulk fluid flow gate 9. The fluid logic device includes a first flow channel 10a for introducing sample into first bulk fluid flow gate 8 through second entry port 8c of first bulk fluid flow gate 8. A second flow channel 11a is in fluid communication with first entry port 8b of first bulk fluid flow gate 8. The second flow channel provides bulk fluid for introducing into first chamber 8e of bulk fluid flow gate 8. First exit port 8a of first bulk fluid flow gate 8 is in fluid communication with second entry port 9c of second bulk fluid flow gate 9. First bulk fluid flow gate 8 further includes second exit port 8d, which may or may not be in communication with another flow channel, a detector, another bulk fluid flow gate, another fluid logic device, etc. Flow channel 11a, which splits within the fluid logic device, is in fluid communication with first entry port 9b of second bulk fluid flow gate 9. First entry port 9b of second bulk fluid flow gate is for introducing bulk fluid into first chamber 9e of second bulk fluid flow gate 9. Second bulk fluid flow gate further includes first exit port 9a and second exit port 9d. Each of first exit port 9a and second exit port 9d may be in fluid communication with a flow channel, a detector, another bulk fluid flow gate, another fluid logic device, etc. Typically, each of the bulk fluid flow gates includes one or more electrodes (not shown) for generating an electric field. Each bulk fluid flow gate may include a single electrode, a pair of electrodes, an electrode array, etc.

In an exemplary separation using the fluid logic device illustrated in FIG. 1c, sample is introduced into the fluid logic device through flow channel 10a. Sample flows into first chamber 9e of the first bulk fluid flow gate 9. Bulk fluid flow is introduced into first chamber 8e of first bulk fluid flow gate through flow channel 11a in fluid communication with first entry port 8b. The electrode(s) (not shown) of the first bulk fluid flow gate generates an electric field. Sample introduced into the first bulk fluid flow gate typically includes charged analyte. Depending on the conditions selected, e.g., electric field strength, bulk fluid flow velocity and/or volume, etc. (as discussed in more detail below), charged analyte typically will migrate towards either second exit port 8d or first exit port 8a. In examples, where operating conditions are selected such that at least some charged analyte migrates toward first exit port 8a, the analyte will exit the first chamber 8e of first bulk fluid flow gate 8 and will enter into second bulk fluid flow gate 9 through second entry port 9c. The electrode(s) (not shown) of the second bulk fluid flow gate generates an electric field. Depending on the operating conditions selected for the second bulk fluid flow gate, e.g., electric field strength, bulk fluid flow velocity and/or volume, etc., analyte introduced into the first chamber 9e of the second bulk fluid flow gate 9 may migrate towards either first exit port 9a or second exit port 9d. In certain examples, one or more of the exit ports of either the first or second bulk fluid flow gates are in fluid communication with a larger system, such as a chromatography system, an analytical system, etc. In other examples, one or more exit ports of either the first or second bulk fluid flow gates are in fluid communication with one or more detectors, such as those listed below. It will be within the ability of the person of ordinary skill in the art to select suitable systems and devices to use in concert with the fluid logic devices disclosed here.

Figure 1D:
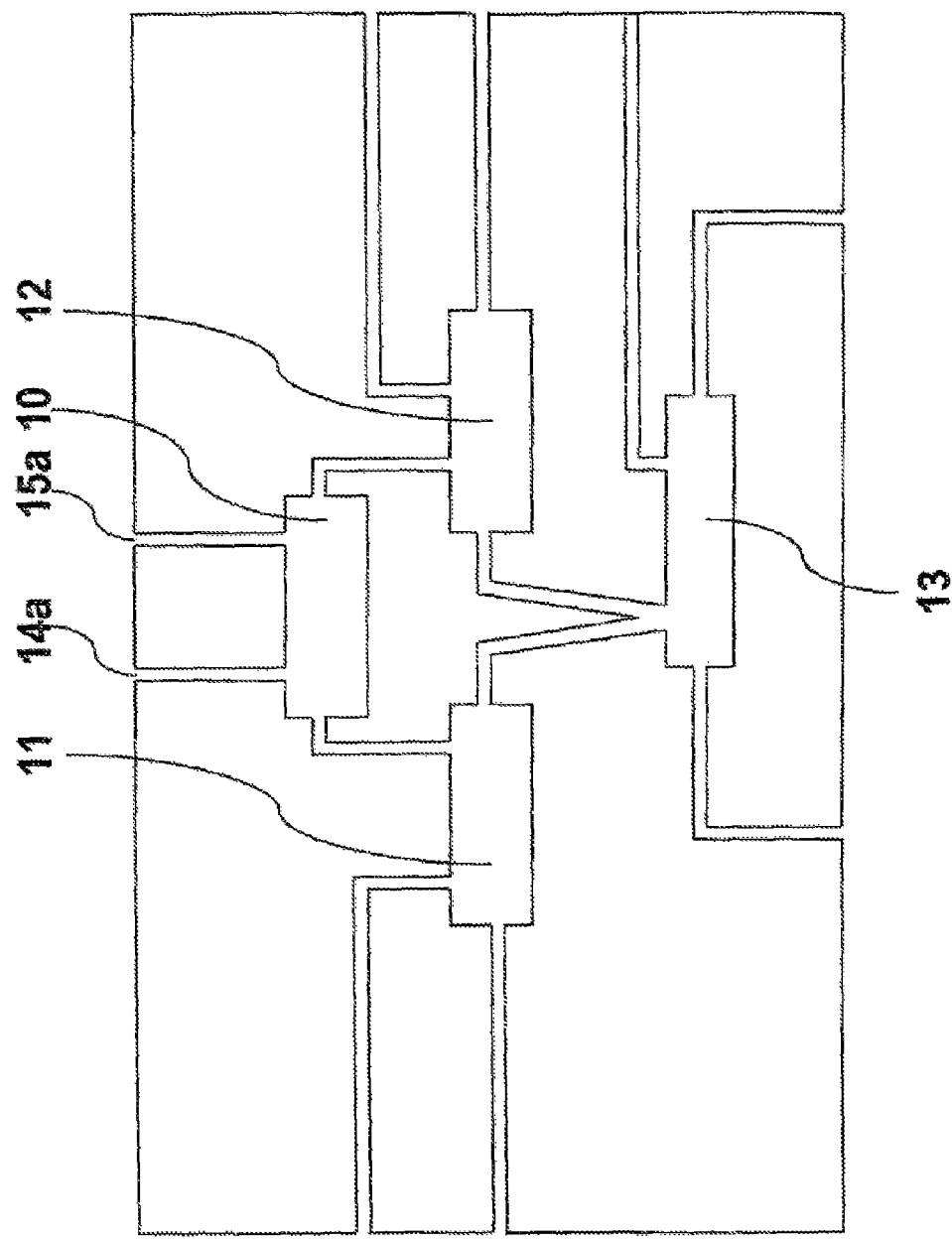
FIG. 1d is a cross-sectional view of a fluid logic device.
Figure 1E:
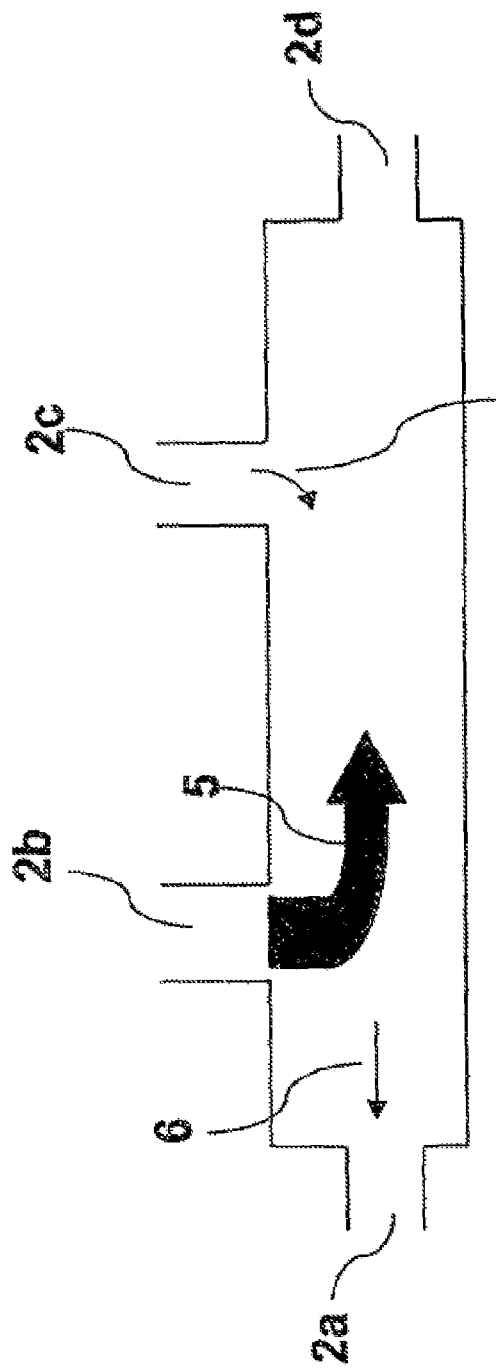

In certain examples a plurality of bulk fluid flow gates are in fluid communication. For examples, FIG. 1d. shows a fluid logic device comprising four bulk fluid flow gates. A first bulk fluid flow gate 10 is in fluid communication with a second bulk fluid flow gate 11. First bulk fluid flow gate is also in fluid communication with third bulk fluid flow gate 12. Each of second bulk fluid flow gate and third bulk fluid flow gate is in fluid communication with fourth bulk fluid flow gate 13. In the example shown in FIG. 1d, sample is introduced into first bulk fluid flow gate 10 through first flow channel 15a and bulk fluid is introduced into first bulk fluid flow gate 10 through flow channel 14a. Sample will migrate and exit either the first or second exit port of the bulk fluid flow gate. The first exit port of first bulk fluid flow gate 10 is in fluid communication with second bulk fluid flow gate 11. The second exit port of first bulk fluid flow gate 10 is in fluid communication with third bulk fluid flow gate 12. The second exit port of second bulk fluid flow gate 11 and the second exit port of third bulk fluid flow gate 12 each is in fluid communication with the second entry port of fourth bulk fluid flow gate 13.

Figure 1F:
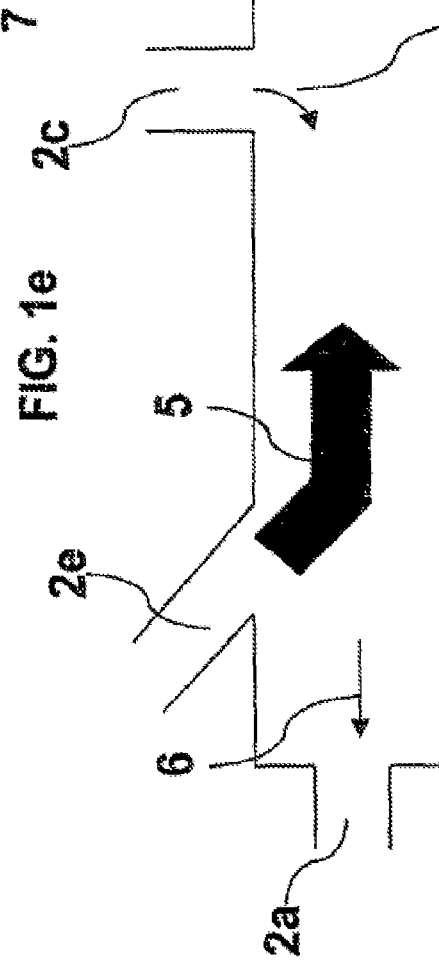

In certain examples, first entry port 2e can be positioned at an obtuse angle to the axial direction of first chamber (see FIG. 1f). A result of such positioning of first entry port 2e at an obtuse angle is that bulk fluid is directed substantially towards first exit port 2d. First exit port 2d experiences greater hydrodynamic resistance that second exit port 2a, which is upstream of first entry port 2e. The velocity of fluid 6, which is upstream of first entry port 2e, is substantially lower than the velocity of bulk fluid flow 5, and fluid 6 flows in a substantially opposite direction to bulk fluid 5. The gating effect is substantially reduced once analyte migrates upstream of first entry port 2e.

In certain examples, the strength of opposing forces, e.g., the hydrodynamic force generated by bulk fluid and the migration force generated by the electric field, are selected to control the rate at which sample migrates in the first chamber. In certain examples, the electric field is kept substantially constant and the velocity and/or volume of bulk fluid is varied until a desired separation is achieved or until analyte migrates at a suitable migration rate. In other examples, the hydrodynamic force is kept substantially constant and the strength of the electric field is selected such that analyte migrates with a suitable migration rate. In yet other examples, both the hydrodynamic force and the migration force are varied such that analyte migrates with a selected migration rate. It will be within the ability of the person skilled in the art, given the benefit of this disclosure, to select suitable bulk fluid velocities and volumes and electric field strengths to control the migration rates of one or more charged analytes.

In accordance with certain examples, the devices disclosed here include a first block comprising a first trough in communication with the first entry port and the second entry port and in communication with the first exit port and second exit port. A second block has a second trough with an inlet for introducing a second liquid to the second trough and an outlet for exiting the second liquid from the second trough. The second trough further comprises an electrode, an electrode pair or an electrode array positioned in the second trough, wherein the first trough and the second trough are substantially coincident and form a channel when the first block is sealed to the second block. A permeable material is provided intermediate the first and second blocks, dividing the channel formed when the first block is sealed to the second block into a first chamber and an electrode housing. The device as such is in the configuration of a discrete unit, or "chip" or consumable cartridge, for example a microfluidic cartridge, which can be swapped out of a suitable receptacle in a laboratory or processing instrument or the like.

Figure 1I:
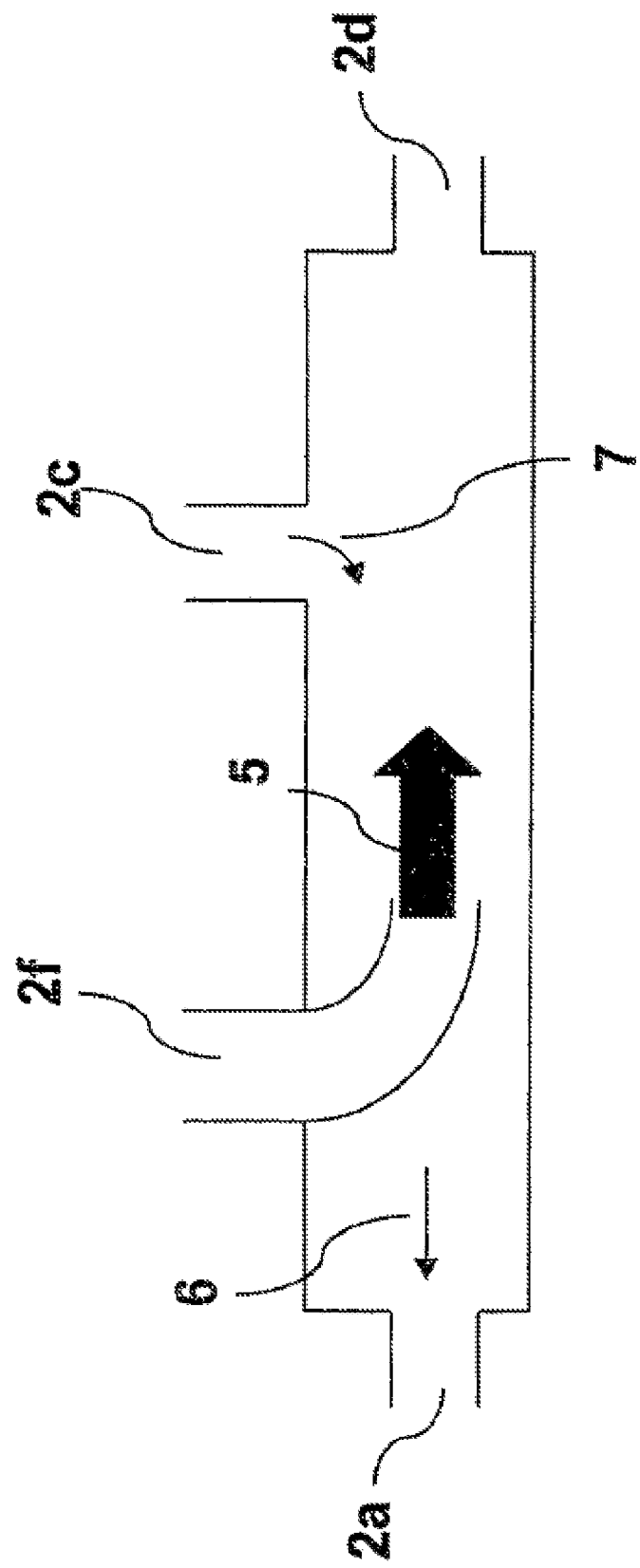

In certain examples, the first chamber of the bulk fluid flow gate includes a non-uniform cross-sectional flow channel, that is to say, the cross-sectional area of the separation chamber varies axially along the channel. For example, FIG. 1g shows a first chamber that has a non-uniform cross-sectional flow channel. The cross-sectional area of the first chamber decreases from second entry channel 2c and towards first exit port 2d. FIG. 1h shows a non-uniform first chamber in which the cross-sectional area decreases from first entry port 2b towards second exit port 2a. FIG. 1i shows a non-uniform first chamber in which the cross-sectional area of first chamber decreases from first entry port 2b to second exit port 2a, and the cross-sectional area of the first chamber also decreases from second entry port 2c towards first exit port 2d. FIG. 1j shows a non-uniform first chamber in which the cross-sectional area decreases at a point between first entry port 2b and second entry port 2c. FIG. 1k shows a non-uniform first chamber in which the cross-sectional area of the first chamber increases from first entry port 2b and towards second exit port 2a, and in which the cross-sectional area decreases from second entry port 2c towards first exit port 2d. The person of ordinary skill in the art, given the benefit of this disclosure, will be able to select these and other non-uniform chambers for an intended use of the bulk fluid flow gate. The first chamber in certain examples has a substantially uniform height (height here meaning the direction normal to the plane of the membrane) and a non-uniform or non-constant width (width here meaning the direction perpendicular to the overall direction of flow and parallel to the plane of the membrane). In other examples, the first chamber has a substantially uniform width and a varying or non-uniform height. Yet other examples employ a first chamber of non-uniform width and non-uniform height. Other examples include a first chamber defined by one or more non-linear walls, for example, a series of faces or facets, some or all having non-uniform dimensions; or wherein the first chamber has a curved cross-section, such as, for example, a half-circular cross-section, that varies axially, as, for example, a half-cone-shaped chamber.

In certain examples, one or more ports of the bulk fluid flow gate may comprise an elbow (see FIG. 1l). For example, first entry port 2f may be in the general shape of a rounded elbow such that bulk fluid introduced into first entry port flows substantially downstream towards first exit port 2d. The ports of the bulk fluid flow gates disclosed here may also include elbows, adapters, fittings, tees, junctions and the like. It will be within the ability of the person of ordinary skill in the art to design suitable ports for use in the bulk fluid flow gates disclosed here.

In certain examples, the electrode(s) of the bulk fluid flow gate generates an electric field that is communicated to the first chamber. Charged analytes introduced into the first chamber typically migrate towards or away from the electrode. Charged species having a charge substantially similar to the charge on the electrode typically migrate away from the electrode, whereas charged species having a charge substantially opposite to the charge on the electrode migrate towards the electrode. In examples where only a single electrode is in communication with the first chamber, it may be necessary to position a second electrode outside of the bulk fluid flow gate for proper operation of the bulk fluid flow gate. One skilled in the art, given the benefit of this disclosure, will be able to select and configure bulk fluid flow gates for an intended use.

In certain examples, the first chamber is in electrical communication with a pair of electrodes. The electrode pair typically is oppositely charged such that analytes migrate towards one of the electrodes of the electrode pair. In a typical arrangement, the negatively charged electrode of the electrode pair is placed downstream near the first exit port and the positively charged electrode is placed upstream near the second exit port. Without wishing to be bound by any particular scientific theory, because many biomolecules are negatively charged at physiological pH, biomolecules will migrate against bulk fluid flow towards the second exit port. One skilled in the art, given the benefit of this disclosure, will be able to select suitable electrode charges in the bulk fluid flow gates disclosed here.

In other examples, the first chamber comprises a uniform or non-uniform tube, with one or more electrodes plated on the interior surface of the tube and coated with a porous, conductive coating. The porous coating is chosen such that it allows small molecules such as buffer ions to pass but prohibits molecules of the size of the analytes from passing through and contacting the electrodes. In those embodiments described here that comprise a porous membrane, the membrane is at least conductive in that it does not prevent the electric field in the chamber and it is porous in the sense that it is permeable to buffer species or the like without allowing contact of the target analyte with the electrodes. In certain embodiments, the membrane does not substantially affect the electric field generated by the electrodes and does not affect the electric field experienced by the separation chamber. In yet other examples, the first chamber comprises a porous, uniform or non-uniform tube, with electrodes plated on the exterior of the tube. The porous tube is likewise chosen to be porous to small molecules and to prohibit passage of molecules of the size of the analyte(s). Other suitable configurations of the bulk fluid flow gate will be readily apparent to the person of ordinary skill in the art, given the benefit of the present disclosure.

In certain examples, the non-uniformity of the first chamber induces a gradient in the electric field. The non-uniformity of the first chamber further leads to a gradient in the hydrodynamic force that exists as a result of flowing bulk fluid through the chamber. It will be within the ability of the person of ordinary skill in the art, given the benefit of this disclosure, to select desired shapes for the chamber, desired electric field strengths and desired hydrodynamic forces.

In other examples, the electrode(s) of the bulk fluid flow gate may be made of suitable conductive materials including but not limited to ionically conductive materials, electronic conductive materials, protonic conductive materials and the like. Exemplary electrodes include, for example, electrodes comprising platinum, palladium, gold, copper, conductive polymer, such as graphite-polymer composites and the like, indium tin oxide ("ITO"), other oxides, and mixtures thereof. Other suitable electrode materials will be readily selected by the person of ordinary skill in the art, given the benefit of the present disclosure.

Figure 2A:
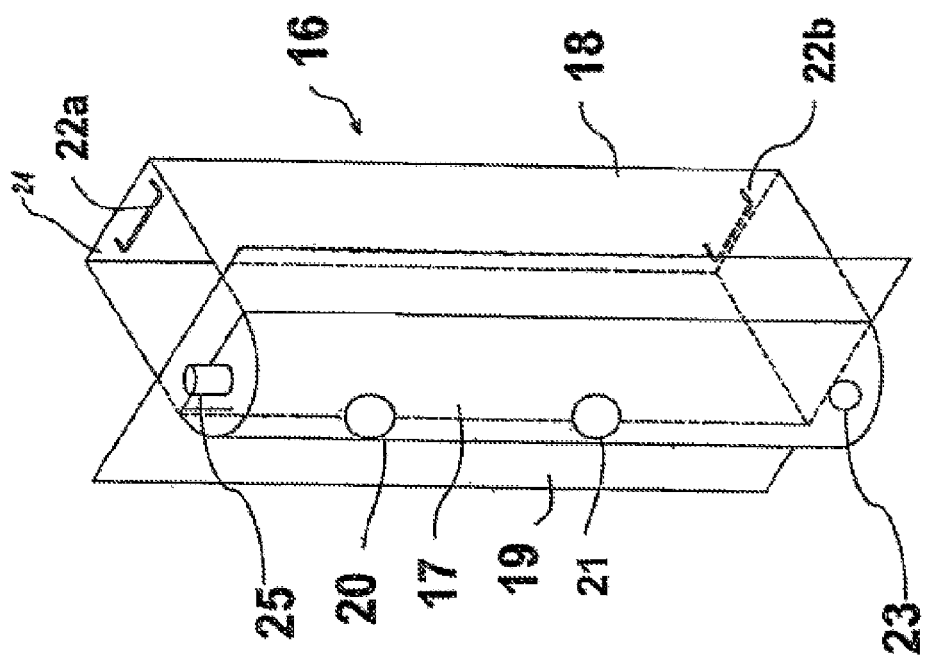
FIG. 2a is a schematic view of a first example of a fluid logic device.

In accordance with other examples, a schematic view of a bulk fluid flow gate is shown in FIG. 2a. The bulk fluid flow gate 16 includes first chamber 17 and an electrode housing 18 separated by permeable member 19. First chamber includes a first entry port 20, a second entry port 21, a first exit port 23 and a second exit port 25. In operation, at least in certain examples, bulk fluid flow flows downward from first entry port 20 through chamber 17 exiting first exit port 23. In certain examples, it may be necessary to flow coolant buffer through electrode housing 18, either upwardly or downwardly. Electrode housing 18 includes a first electrode 22a and a second electrode 22b. As shown in FIG. 2a, the electrodes can be positioned at opposite ends of chamber 17 and permeable member 19. In certain examples when the device of FIG. 2a is used to purify a sample or separate analytes in a sample, sample is introduced into second entry port 21 and bulk fluid is introduced into first entry port 20. Analyte that migrates upward towards electrode 22a can exit the first chamber through second exit port 25, whereas analyte that migrates toward electrode 22b can exit the first chamber through first exit port 23. As discussed in more detail below, the rate of analyte migration typically depends on the selected hydrodynamic force generated by bulk fluid flow and the selected electric field strength.

Figure 2B:
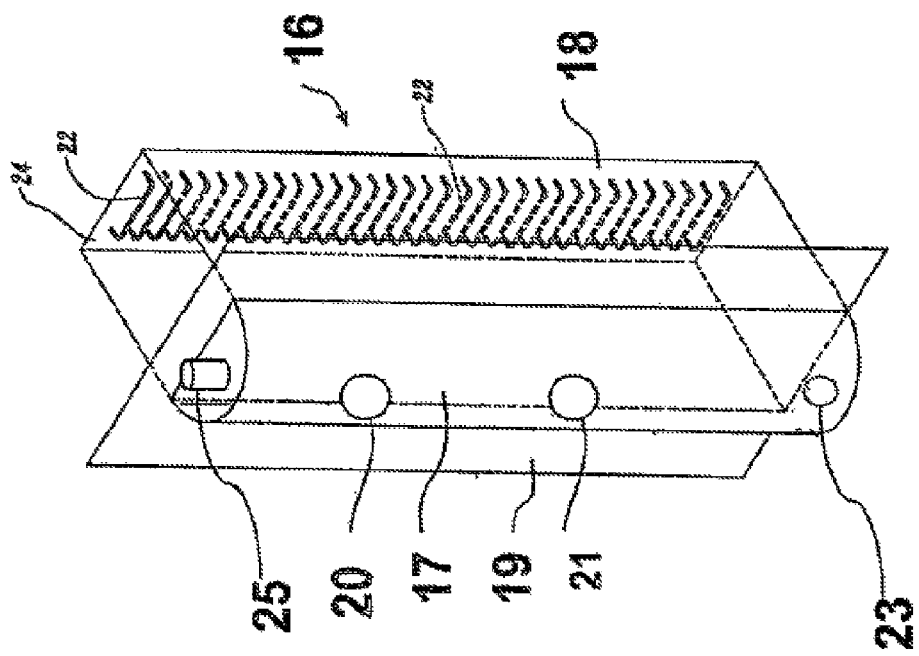
FIG. 2b. is a schematic view of a second example of a fluid logic device.

In accordance with another example, a schematic view of a second example of a bulk fluid flow gate is shown in FIG. 2b. The bulk fluid flow gate 16 includes first chamber 17 and an electrode array 22 separated by permeable member 19. First chamber includes a first entry port 20, a second entry port 21, a first exit port 23 and a second exit port 25. In operation, at least in certain examples, bulk fluid flow flows downward from first entry port 20 through chamber 17 exiting first exit port 23. In certain examples, it may be necessary to flow coolant buffer through electrode housing 18, either upwardly or downwardly. Electrode housing 18 includes an electrode array 22. As used herein, the term "electrode array" refers to a plurality of electrodes arranged so as to generate an electric field gradient in the separation chamber. The electric field generated by the electrode array can be DC, AC, or otherwise modulated in time including asymmetric (out of phase) field modulation. The specific nature of the electrode (i.e., size and shape) is not critical. Suitable electrodes include rod-shaped, pin-shaped and staple-shaped electrodes, among others. In one example, the electrode array includes a linear array of electrodes (e.g., 50 electrodes arranged linearly) along an axis parallel to the direction of analyte migration. In addition to arrays having electrodes arranged in line with even spacings from one to the next, suitable arrays also include arrays in which the electrodes are not in line and which are not separated by even spacings. Other configurations of electrodes, including two-dimensional electrode arrays, are also within the scope of the devices and methods. Two-dimensional arrays include arrays having rows and columns of electrodes. The second chamber in certain preferred examples includes more than one electrode array, for example two electrode arrays on opposite sides of the electrode chamber. Suitable electrode array configurations will be readily apparent to the person of ordinary skill in the art, given the benefit of the present disclosure, for example electrode array configurations presented in U.S. Pat. No. 6,277,258, which is incorporated by reference herein in its entirety for all purposes.

In certain examples, each electrode of the array is individually controlled to provide an electric field gradient that can be dynamically controlled (i.e., maintained and adjusted during the course of analyte migration, focusing and/or separation). Control can be manual from the device controller, manually from the device's associated computer, or automatically from the computer once the computer has received feedback from a monitor, such as an optical monitor, for example a video signal, or other suitable monitoring device, following analyte migration or focusing. The controller can sense the electrode's voltage and reset its voltage to its initial setting. Such monitoring allows for computer detection of various peaks, optimization of the separation by locally adjusting the field gradient to tease separated peaks apart, and then pull off those peaks that were selected by the operator either before or during a separation. Suitable configurations of the electrodes, controls, computer equipment and the like will be readily apparent to those of ordinary skill in the art, given the benefit of the present disclosure, for example configurations presented in U.S. Pat. No. 6,277,258, which as noted above is incorporated by reference herein in its entirety for all purposes.

In accordance with other examples, the electronically generated field can take on arbitrary shapes including logarithmic profiles, exponential profiles, profiles taking shape after applying one or more apodization function to the electric field, steps, and even locally reversed gradients, for example, to elute proteins. The field shape can be monitored and maintained by computer and modified "on-the-fly" on a point-by-point basis, both spatially and temporally. During a run the operator can optimize the local properties of the field to sharpen an individual band, move a band to an exit or offtake port or set up a moving gradient to elute one or more bands from the chamber. With online monitoring, for example optical monitoring such as UV/Visible monitoring, or potentiometric monitoring, in place, the operator could be replaced by a computer programmed to detect focused peaks and automatically adjust the field shape to optimize the separation and, when necessary, offload products. Suitable monitoring systems and configurations will be readily apparent to the person of ordinary skill in the art, given the benefit of the present disclosure.

As discussed above, in certain examples, the first chamber and the electrode housing in certain examples are separated by a permeable material. Suitable permeable materials, for example, allow ions to pass through the permeable material while (1) desired analytes, for example, macromolecules such as biomacromolecules, are retained in the first chamber; while (2) undesired contaminants can flow, or be dialyzed, out of the first chamber; and (3) desired molecules, for example, buffer ions, can flow, or be dialyzed, into the first chamber. In certain examples, the permeable membrane is conductive to heat and buffer ions but not to bulk fluid flow. The permeable membrane advantageously serves to isolate the electrodes from the first chamber to avoid disruption of bulk fluid flow by gas generation or denaturation of charged analyte by contact with the electrodes. Suitable permeable materials include permeable membranes such as dialysis membranes and ion-exchange membranes. Other suitable permeable materials will be readily apparent to the person of ordinary skill in the art, given the benefit of the present disclosure.

In certain examples, as discussed above, the electrode housing is non-uniform. As used herein, "non-uniform" refers to a housing or chamber that has a non-uniform cross-section, that is to say, the cross-sectional area of the chamber varies axially along the length of the chamber, length referring to the direction in which fluid flows through the separation chamber. In examples using a non-uniform electrode housing, the electrode housing has a cross-section that varies axially along the length of the housing. The electrodes may be operative to generate an electric field in the electrode housing, where the non-uniformity of the electrode housing induces a gradient in the electric field. This electric field gradient is communicated to the first chamber by the porous membrane. The electrode housing in certain examples is substantially uniform, that is, has a uniform cross-section flow channel. The electrode chamber in certain examples has a substantially uniform depth (depth here meaning the direction normal to the plane of the membrane) and a non-uniform or non-constant width (width here meaning the direction perpendicular to the overall direction of flow and parallel to the plane of the membrane). In other examples, the electrode housing has a substantially uniform width and a varying or non-uniform depth. Still other examples employ an electrode housing of non-uniform width and non-uniform depth. Other examples include an electrode housing defined by one or more non-linear walls, for example, a series of faces or facets, some or all having non-uniform dimensions; or wherein the electrode chamber has a curved cross-section, such as, for example, a half-circular cross-section, that varies axially, as, for example, a half-cone-shaped housing with either straight or curved walls in the axial direction. Other suitable non-uniform electrode housing configurations will be readily apparent to those of skill in the art, given the benefit of the present disclosure.

In some examples, devices disclosed here are useful in migration, focusing and separation of charged analytes. In certain examples, the migrating analytes can be eluted from the device through either the first or second exit ports, or other ports positioned suitably along the first chamber, e.g. one or more sampling ports positioned upstream or downstream of bulk fluid flow. Analytes can be eluted from the first chamber by electric field, pressure, vacuum, or other motive force or may elute as bulk fluid exits the first chamber.

Certain examples of the devices disclosed here can further include a monitoring feature which detects analyte migration. Suitable analyte detection includes optical and potentiometric methods. Optical methods include providing a clear window in the first chamber so that an operator can observe the focusing of the bands directly, and further include optical methods such as UV/Visible spectroscopy that can be monitored by the operator or by computer. Optional integration of the signal put forth from the monitoring feature with software allows automation and computer optimization of analyte loading, separation, and elution steps.

In other examples, the device can be operated in a continuous mode in which analyte for focusing and/or separation is continuously loaded into the first chamber and focused to sampling ports, or allowed to migrate to exit ports, where the analytes are continuously eluted. In the alternative, the device can be operated in a batch mode in which the analyte is loaded in its entirety and then allowed to migrate to one or more exit ports and/or sampling ports.

Another example of a bulk fluid flow gate as described above is shown in FIGS. 3A-6B. FIG. 3A shows an exploded view of the device including front and rear portions. An elevation view of the device is shown in FIG. 4, and forward and rear plan views of the device as illustrated in FIGS. 5A and 5B, respectively. A cross-sectional view of a portion of a representative device illustrating the first chamber, permeable membrane, and electrode housing is shown in FIGS. 6A-B.

Figure 3B:
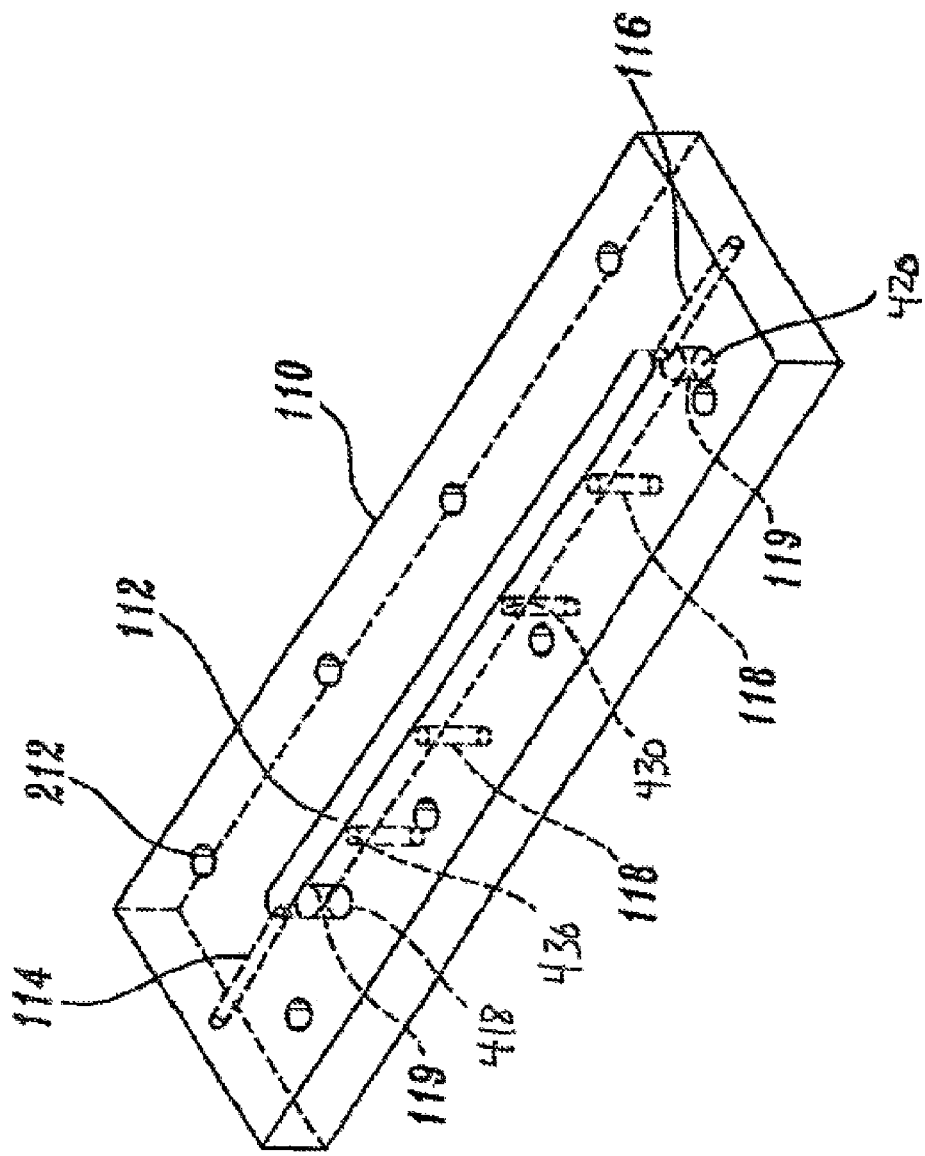
FIGS. 3B-3E are schematic perspective views of selected components of the device illustrated in FIG. 3A.
Figure 3C:
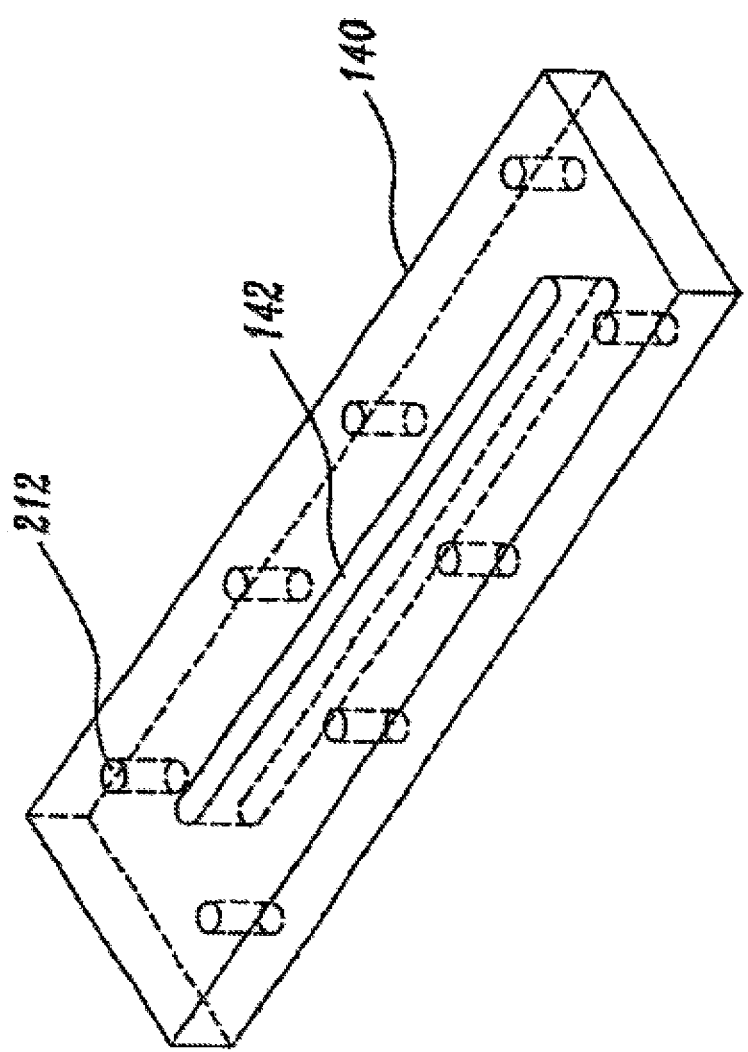
Figure 3D:
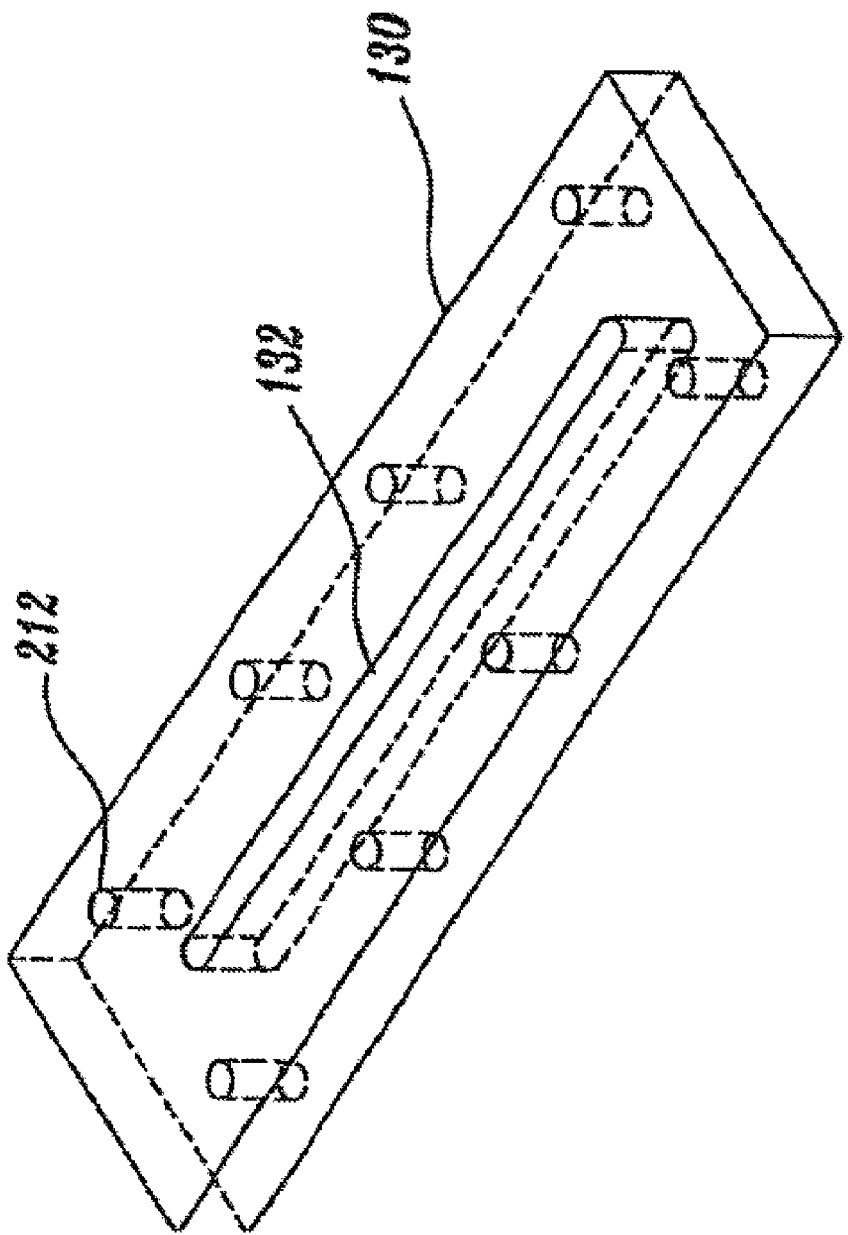
Figure 3E:
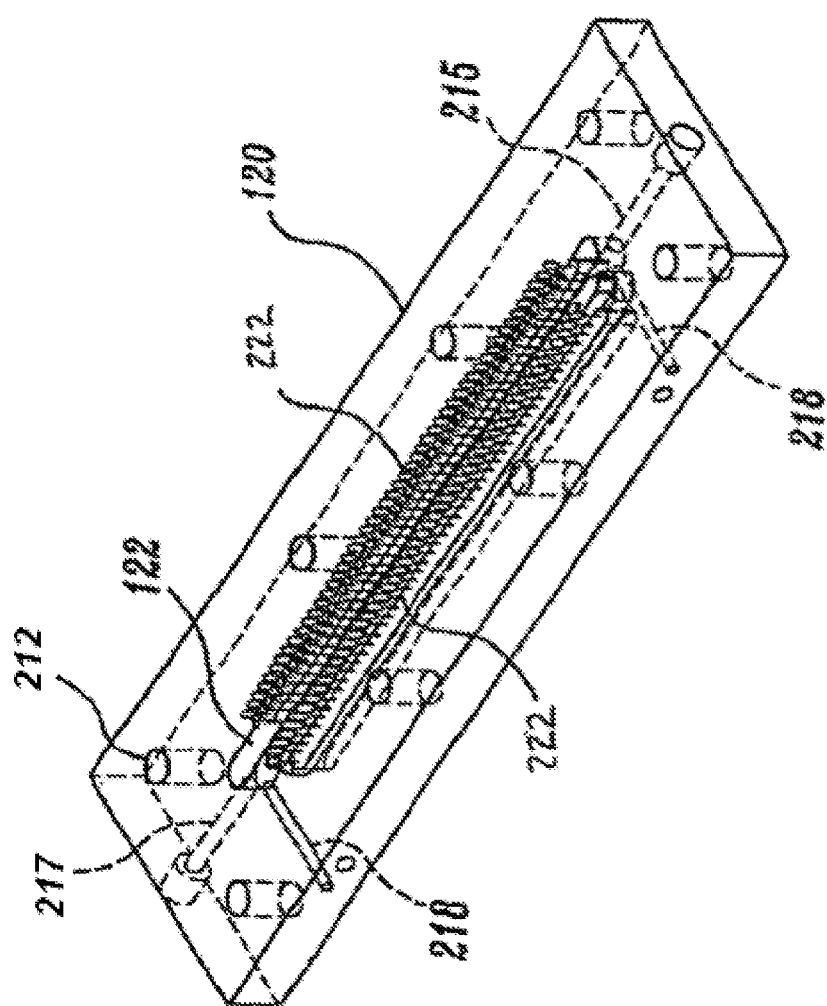
Figure 4:
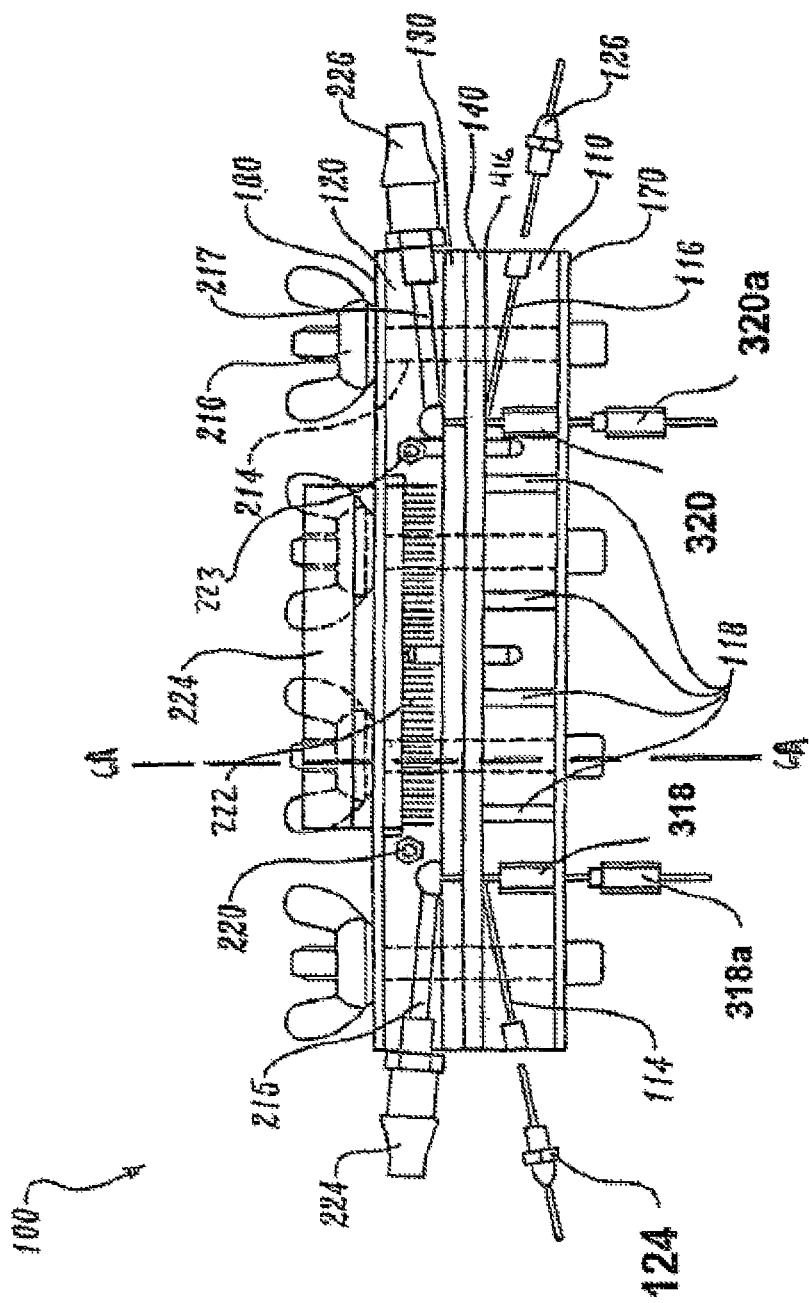
FIG. 4 is an elevation view, partly in section, of the device of FIGS. 3A-3E in assembly.

A representative bulk fluid flow gate including a first chamber is shown in FIGS. 3A-E. The example illustrated in FIG. 3A includes side-by-side electrode arrays. Referring to FIG. 3A, device 100 has basic components including first block 110 and second block 120 separated by intermediate sheets 130 and 140. Permeable member 416 is intermediate block 110 and sheet 140. Blocks 110 and 120 and intermediate sheets 130 and 140 are formed from machinable materials. Preferably, blocks 110 and 120 and intermediate sheet 130 are formed from PLEXIGLAS and sheet 140 is formed from TEFLON. In one example, each component includes a plurality of apertures 212 that are coincident with the apertures of the other components when the components are assembled. Apertures 212 receive bolts 214 (see FIG. 4) for securing the assembled components and assist in sealing the assembly. As shown in FIG. 4, the components are secured through tightening nuts 216 on bolts 214.

In certain examples, to form the bulk fluid flow gate, first block 110 and second block 120 include troughs 112 and 122, respectively. Trough 122 includes the electrode arrays, each array comprising a plurality of electrodes 222. In other examples, trough 122 may include a single electrode or a pair of electrodes. Sheets 130 and 140 include apertures 132 and 142, respectively. When the components are assembled, troughs 112 and 122 and apertures 132 and 142 are coincident and form a portion of the bulk fluid flow gate 410. Intermediate sheet 140 and block 110 is permeable member 416 which divides bulk fluid flow gate 410 into first chamber 412 and electrode housing 414.

First block 110 includes conduits 114 and 116 which terminate in opposing ends of trough 112. Conduits 114 and 116 serve as the first exit port and the second exit port. First block 110 further includes channel 430 which terminates in trough 112 and which provides for introduction of bulk fluid into the device. Channel 436 also terminates in trough 112 and provides for introduction of sample into the first chamber. Other channels, e.g., channels 118 and 119, may be present for sampling. Channels 118 and 119 also terminate in trough 112 and provide for removal and/or introduction of in the first chamber. Second block 120 includes conduits 215 and 217, which terminate in opposing ends of trough 122. These conduits serve to introduce and exit liquid flow (e.g., coolant) through the electrode housing. In examples of the device that include an electrode pair in addition to the electrode array, second block 120 further includes channels 218 which terminate in trough 122. Channels 218 receive electrodes 220 and 223, which like the electrode array, are in electrical communication with liquid in the electrode housing when the device is in operation.

An example of an assembled device is illustrated in FIGS. 4 and 5. Referring to FIG. 4, device 100 includes blocks 110 and 120 and sheets 130 and 140, and permeable member 416. First entry port 320 includes adapter 320a, e.g., a connecting device. Second entry port 318 also includes an adapter 318a. First exit port 114 is positioned upstream of first entry port 320. Second exit port 116 is positioned downstream from first entry port 320. Optional sampling ports 118 are also shown. Connector 224 leads to the device's controller and provides current to the electrode(s) or the electrode array. The representative device further includes first and second plates 170 and 180, respectively, which overlie the outward surfaces of blocks 110 and 120, respectively. Plates 170 and 180 can reinforce the assembly. Plates 170 and 180 are preferably steel plates. The bulk fluid flow gate shown in FIG. 4 generally comprises a laminate structure. Suitable laminate structures, and methods for making such laminate structures, are disclosed in the commonly assigned published PCT applications incorporated by referenced above.

FIGS. 6A and 6B are cross-sectional views of a portion of the representative device described above, taken through line 6A-6A in FIG. 4 and through line 6B-6B in FIG. 5. Referring to FIG. 6B, device 100 includes blocks 110 and 120 and sheets 130 and 140. Intermediate block 110 and sheet 140 is permeable material 416 which divides the bulk fluid flow gate into first chamber 412 and electrode housing 414. Sheet 140 serves as a spacer for adjusting the depth of electrode housing 414 and, the thickness of sheet 140 can be varied as desired. Sheet 140 is a resilient sheet and also serves to seal block 110 to the remaining components of the assembly. Intermediate sheet 140 and sheet 130 is a sealant layer 150. Sealant layer 150 includes a sealant that effectively joins sheet 140 to sheet 130 and prevents fluid from escaping the electrode housing. Intermediate block 120 and sheet 130 is adhesive layer 160. Adhesive layer 160 includes an adhesive that effectively joins sheet 130 to block 120.

A representative device including a bulk fluid flow gate is formed from two blocks of 15×6×1.2 cm$^3$ PLEXIGLAS and a 0.3 cm thick TEFLON spacer. The front block, which houses the first chamber has a trough 8×0.1×0.05 cm$^3$ machined into it, the rear block, which houses 50 controllable electrodes, has a trough 6.4×0.3×1.5 cm$^3$, and the spacer has a 6.5×0.2 cm$^2$ slot machined through it. The trough in the front block is isolated from the spacer by the permeable material. The rear trough and slot admit a recirculating buffer, e.g., coolant, that can have the same composition as the bulk fluid or may be different. Because the coolant is in contact with the separation column by a permeable material, the coolant can also be used to dialyze the running buffer to exchange salts or other low molecular weight analytes. The coolant inlet and outlet are shown in FIGS. 4 and 5.

Cooling of the electrode chamber and/or of the device overall can be provided by any suitable heat removal system. Exemplary systems include flows of cooling fluid, in the electrode chamber, thermoelectric coolers, refrigeration systems relying upon the evaporation of a refrigerant fluid (typically then recirculated through a condenser, etc.), etc. In accordance with certain exemplary embodiments a coolant buffer is employed. Outside of the electrode housing, the coolant buffer can be circulated through a glass heat-exchange reservoir submerged in an ice bath. From here the coolant is introduced into the bottom of the bulk fluid flow device and is passed over the electrodes. In micro-scale and certain larger embodiments of the devises and methods disclosed here, such flow can be at rate of about 500 mL/min to 1500 mL/min, e.g., about 900 mL/min. Flow can be controlled using, e.g., a centrifugal pump (Cole-Parmer) or other suitable pumps and devices, e.g., peristaltic pumps and the like. In micro-scale and certain larger embodiments of the devises and methods disclosed here, a syringe pump typically controls the flow of bulk fluid through the chamber. In micro-scale embodiments of the devises and methods disclosed here, exemplary flow rates are 0-20 microliters per minute. In micro-bore scale embodiments of the devises and methods disclosed here, exemplary flow rates are 20-100 microliters per minute. In analytical scale embodiments of the devises and methods disclosed here, exemplary flow rates are 1.0 mL/min. to 2.0 mL/min. In preparative scale embodiments of the devises and methods disclosed here, exemplary flow rates are 2.0 to 20.0 mL/min. In process scale embodiments of the devises and methods disclosed here, exemplary flow rates are 20 mL/min and higher. The bulk fluid enters the first chamber through first entry port and exits the first chamber thorough first exit port. In certain examples, all lines are PEEK with flangeless fittings; sample can be loaded through a 10-µL loop on a six-port injection valve (Upchurch) which is in fluid communication with the second entry port.

In certain examples, the electrodes can be made from 0.25-mm-o.d. platinum wire (Aldrich Chemical), mounted in the rear PLEXIGLAS block with a 0.05-in. pitch, and are connected to a SCSI ribbon cable, or other suitable cables such as IDE cables, USB cables, IEEE1394 cables, SATA cables, etc., using SMS-series microstrips (Samtec). Each of the SCSI leads is connected to its own printed-circuit (PC) monitor/controller board mounted on the wire wrap motherboard. Each monitor/controller board is segregated into three areas: high voltage, monitoring, and control. The high-voltage area isolates the electrode voltages, which can be as high as 600 V, from the relatively sensitive electronics used to measure and adjust the electrode voltages. The monitor area of each PC board scales down the electrode voltage by about 100× and sends this signal to a commercial thermocouple board which digitizes the signal before sending it to the computer. The computer scans all 50 electrodes, compares these readings with the programmed profile, and sends a digital signal to a set of 50 DACs which tell the optical isolators to adjust the effective resistance of high-voltage line to reduce the departure of the measured electrode voltages from the programmed voltage profile. A complete scan/control cycle of the 50 controllers is taken every second. Each of the 50 controllers is mounted vertically on a wire-wrapped motherboard; power to the controllers' motherboard is drawn from the computer. A 600-V power supply (Xantrex) provides current to the column's 50 high-voltage electrodes via the 50 voltage controllers.

In certain examples, the device is operated as follows. After the recirculating coolant has reached operating temperature and the first chamber has been cleaned, e.g., with 7 M urea, and equilibrated with bulk fluid, a suitable amount of sample, e.g., 10 µL, is injected into the chamber using a standard sample loop in communication with second entry port. Before sample reaches the first chamber, the controller is booted using a default voltage pattern and the power supply is brought up to a voltage in the range 200-600 V. The operator then selects the initial electric field or electric field gradient, and the computer program adjusts the electrode voltages until this gradient is attained, typically less than 5 min. from a "cold" start. Where the electrophoretic mobilities or charge to mass ratios of two analytes are sufficiently close, the electric field gradient alone may be insufficient to separate them. Without wishing to be bound to any particular scientific theory, it is currently understood that analytes are separated by the methods and devices disclosed here on the basis of their molecular weights by effectively applying different hydrodynamic forces to differently sized molecules; that is to say, due to bulk fluid flow and/or changes in the volume and velocity of bulk fluid flow.

Although the above examples illustrate the use of linear electric field gradients, the software can be modified to allow point-by-point adjustment of the field including reversing the field to aid in migration or elution of fractionated bands, isolating and mobilizing a single protein band, or stepping the gradient to improve processing capacity. In addition, because the electronic controller and the technique are largely independent of chamber capacity, there is no reason it cannot be applied at larger or smaller scales.

Certain examples of the bulk fluid flow gate provided by the methods and devices disclosed here optionally rely in part on field gradient control, which includes hardware and software. Representative gradient control hardware and software are discussed below.

Figure 10:
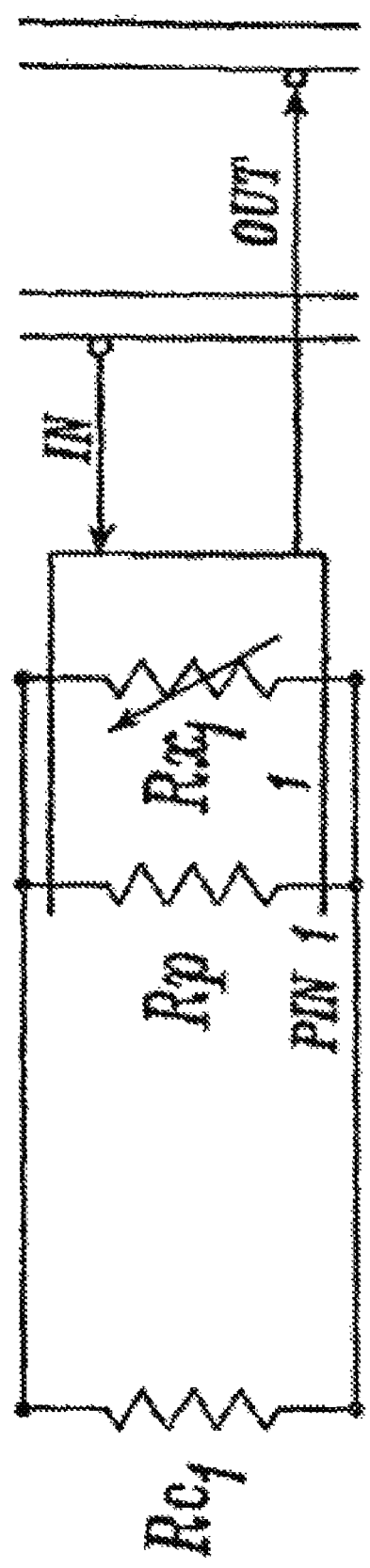
FIG. 10 is a schematic representation of the resistance between two adjacent electrodes in another example of the methods and devices disclosed here.
Figure 11:
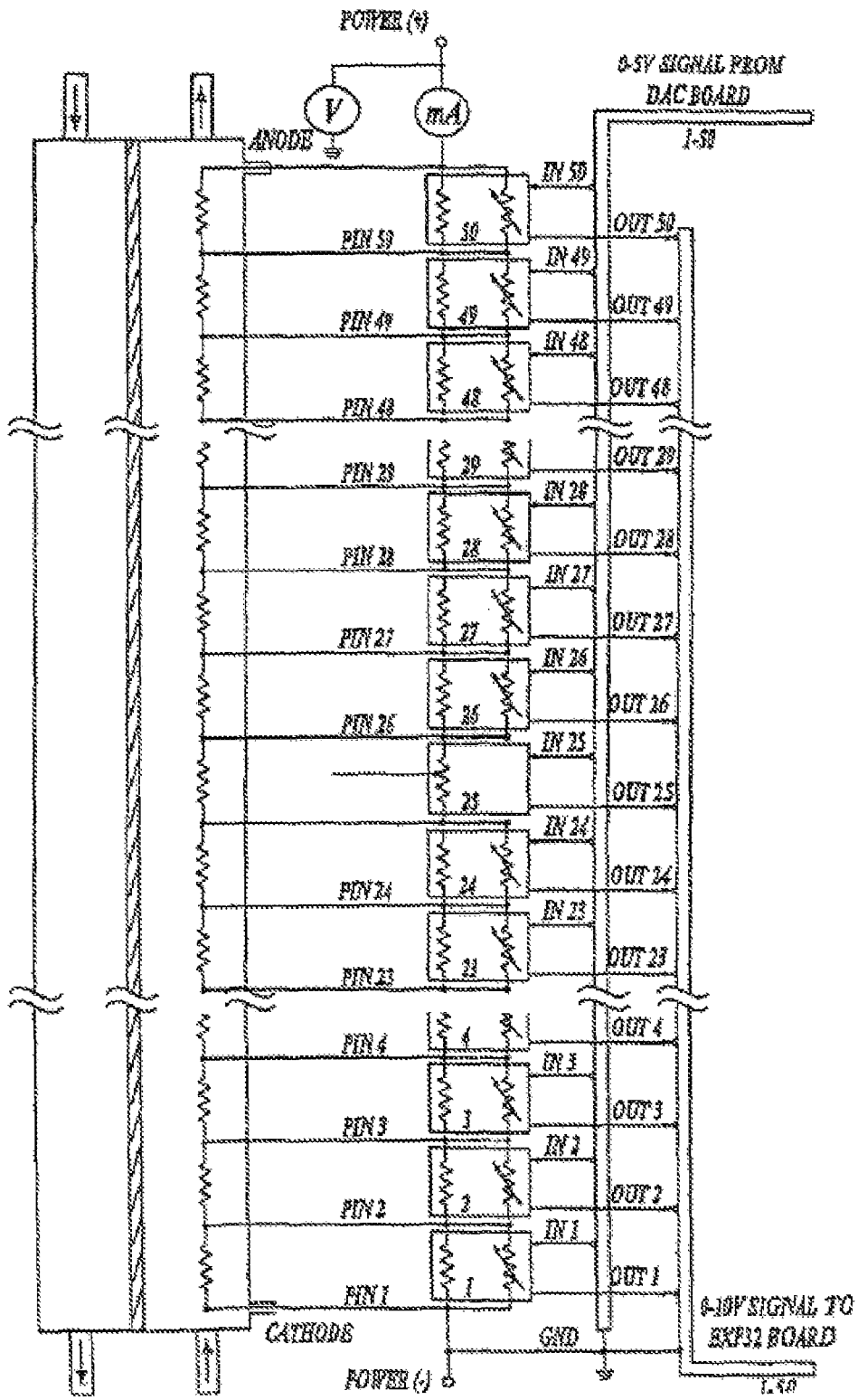
FIG. 11 is a schematic diagram of a representative electric field gradient focusing gradient control model of an example of the methods and devices disclosed here.

The control circuits are designed to manipulate the field gradient by adjusting the effective electrical resistance between two adjacent electrodes (see FIG. 10). In one example, each pair of electrodes is connected to one of the 50 controller units. A schematic of such an example is shown in FIG. 11, in which the blocks with dash line frames are controller units and each of the controller units handles the data acquisition and the resistance control of two adjacent electrodes.

The electrical resistance between two adjacent electrodes $R_i$ is determined by the sum of the resistance of three parallel resistors, $Rc_i$, $Rp_i$, and $Rx_i$. Note that the buffer between electrodes is considered as a resistor $Rc_i$.

$$R_i = \frac{Rc_i \cdot Rp_i \cdot Rx_i}{Rc_i \cdot Rp_i + Rc_i \cdot Rx_i + Rp_i \cdot Rx_i} \quad (1)$$

The resistors $Rp_i$ are used for protective purpose and have 1 MΩ resistance. Because $R_p \gg Rc_i$, $R_p \gg Rx_i$. Equation (1) can be simplified as $$R_i = \frac{Rc_i \cdot Rx_i}{Rc_i + Rx_i} \quad (2)$$

By changing each $Rx_i$, the circuits adjust each $R_i$ indirectly. In accordance with Ohms Law, the potential drop between two electrodes is determined by the resistance between them when the total current is constant. The potential drop between the two adjacent electrodes is given by $$V_i = V_{total} \cdot \frac{R_i}{\sum_i^{50} R_i} \quad (3)$$

Since the field strength is proportional to the potential drop with the electrodes equally spaced, the field strength point by point can be manipulated by adjusting each Rxi, independently.

$$E_i = \frac{V_i}{d} = \frac{V_{total}}{d} \cdot \frac{R_i}{\sum_i^{50} R_i} \quad (4)$$

where d is the distance between the two adjacent electrodes. An electric field gradient in any shape, linear or nonlinear, continuous or stepwise, can be produced with a limitation to the conductivity of the buffer. Note that the resistance between two parallel-connected resistors is always less than any one of them, in other words, $R_i < Rc_i$ must be satisfied.

The person of ordinary skill in the art, given the benefit of this disclosure, will recognize that there is more than one group of $R_i$ that satisfies Equation 4. In other words, different groups of $Rx_i$ can be used to establish the same field gradient with the total current going through the chamber arbitrarily. There is no unique equilibrium state.

Figure 8:
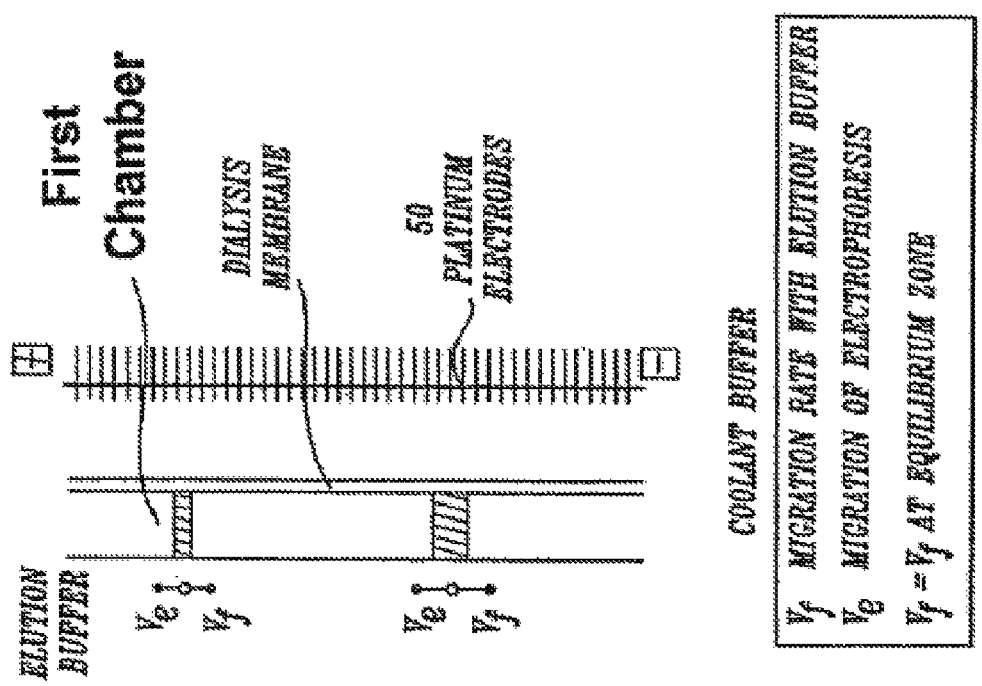
Figure 9A:
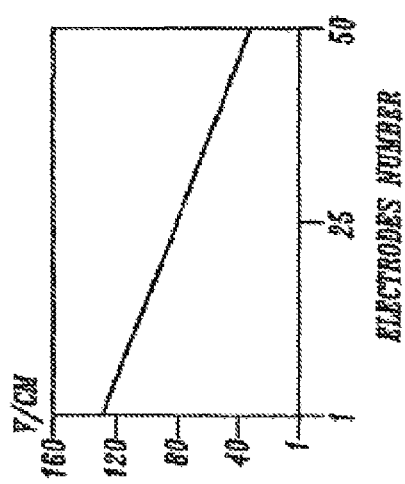
FIGS. 9A and 9B each is a graphical representation of the field strength profile and potential profile, respectively, of a linear field gradient (15.5 v/cm.sup.2) in accordance with another example of the methods and devices disclosed here.
Figure 9B:
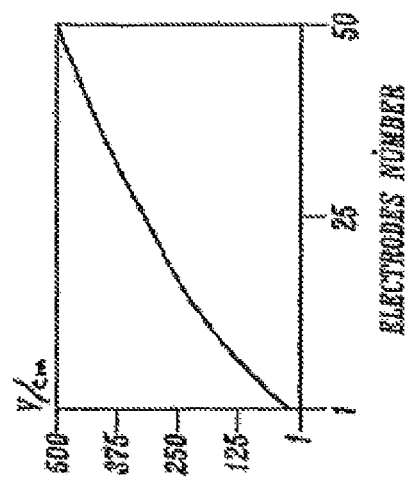

In certain examples, dynamic electric field gradients are created by a computer-controlled external circuit, which manipulates the field strength between each pair of adjacent electrodes, as exemplified in FIG. 8. Varying field strength along the first chamber can thus be achieved. FIGS. 9A and 9B are graphical representations of linear electric field gradients so generated.

Figure 12:
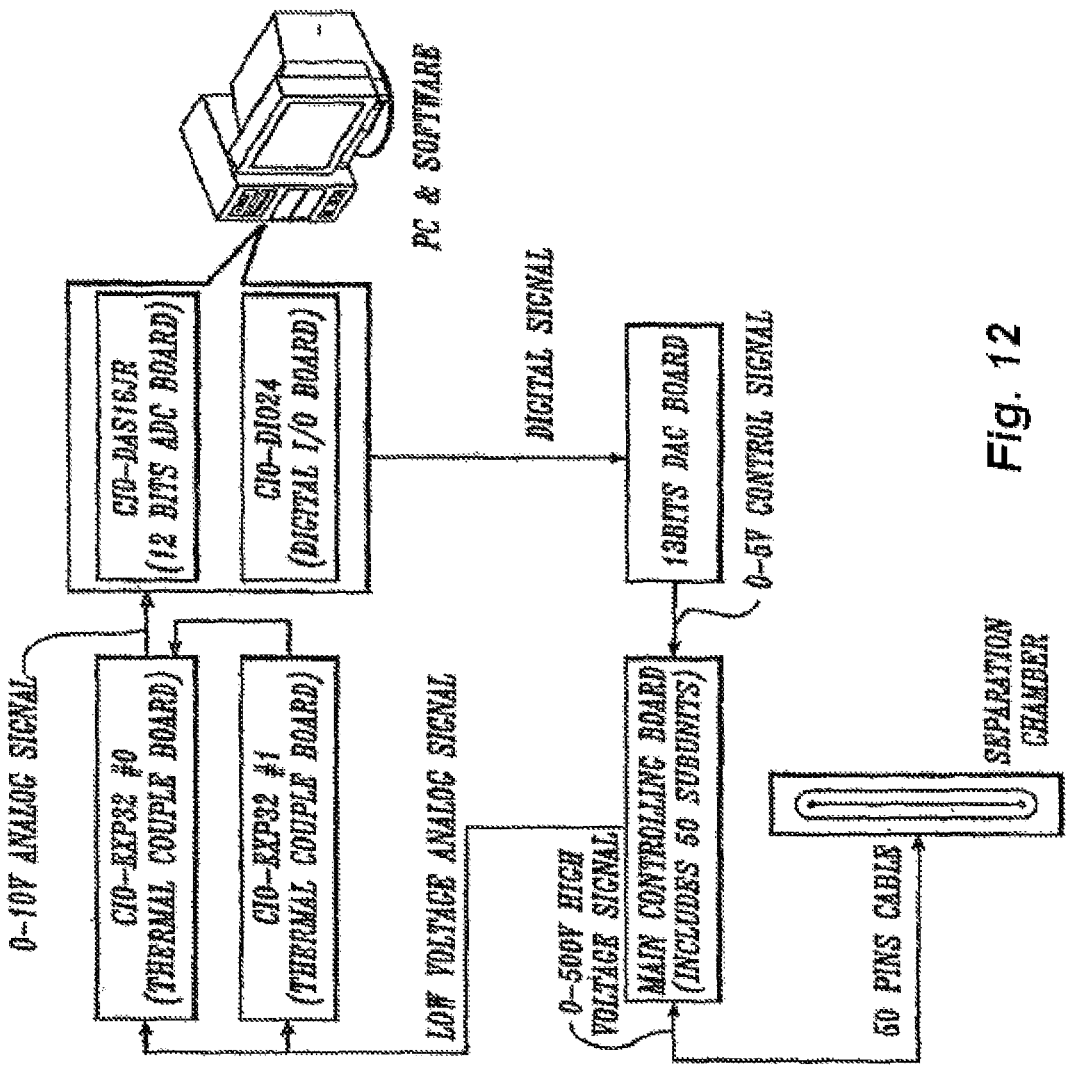
FIG. 12 is a schematic diagram of a representative electric field gradient focusing gradient control circuits.

Representative gradient control circuits are shown schematically in FIG. 12. The blocks represent electronic boards, the lines represent standard ribbon cables, e.g., IDE cables, USB cables, IEEE1392 cables, serial cables, parallel cables, SATA cables, SCSI cables and the like. Referring to FIG. 12, the PC monitor/controller board and the 13-bit DAC board were built in our laboratory. Some modifications have been made for better performance. The data channels between the two CIO-EXP32 boards and the CIO-DAS16Jr boards are programmed rather than being physically connected. CIO-DAS16Jr and CIO-DIO24 are plugged into extension slots of the PC. The two thermocouple boards CIO-EXP32, the 16-channel ADC board CIO-DAS16/Jr and the 24-channel Digital I/O board CIO-DIO24 were purchased from ComputerBoards, Inc. Standard SCSI ribbon cables are used to connect all the boards. There are 50 controller units plugged into the mother board. Each unit corresponds to one pair of electrodes. The whole system was grounded to protect the circuits from unexpected shock.

Figure 13:
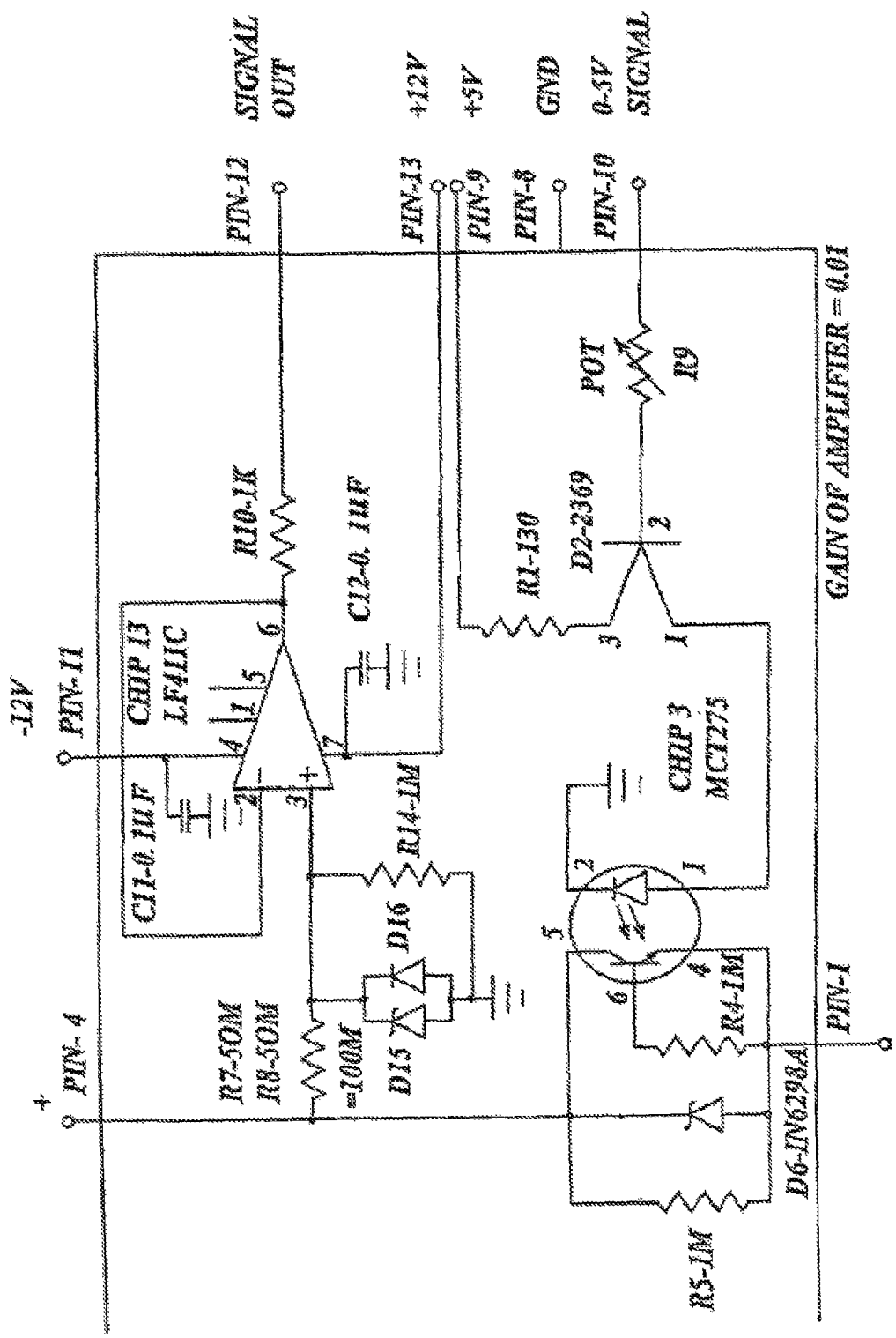
FIG. 13 is a circuit diagram of a representative controller unit.
Figure 14:
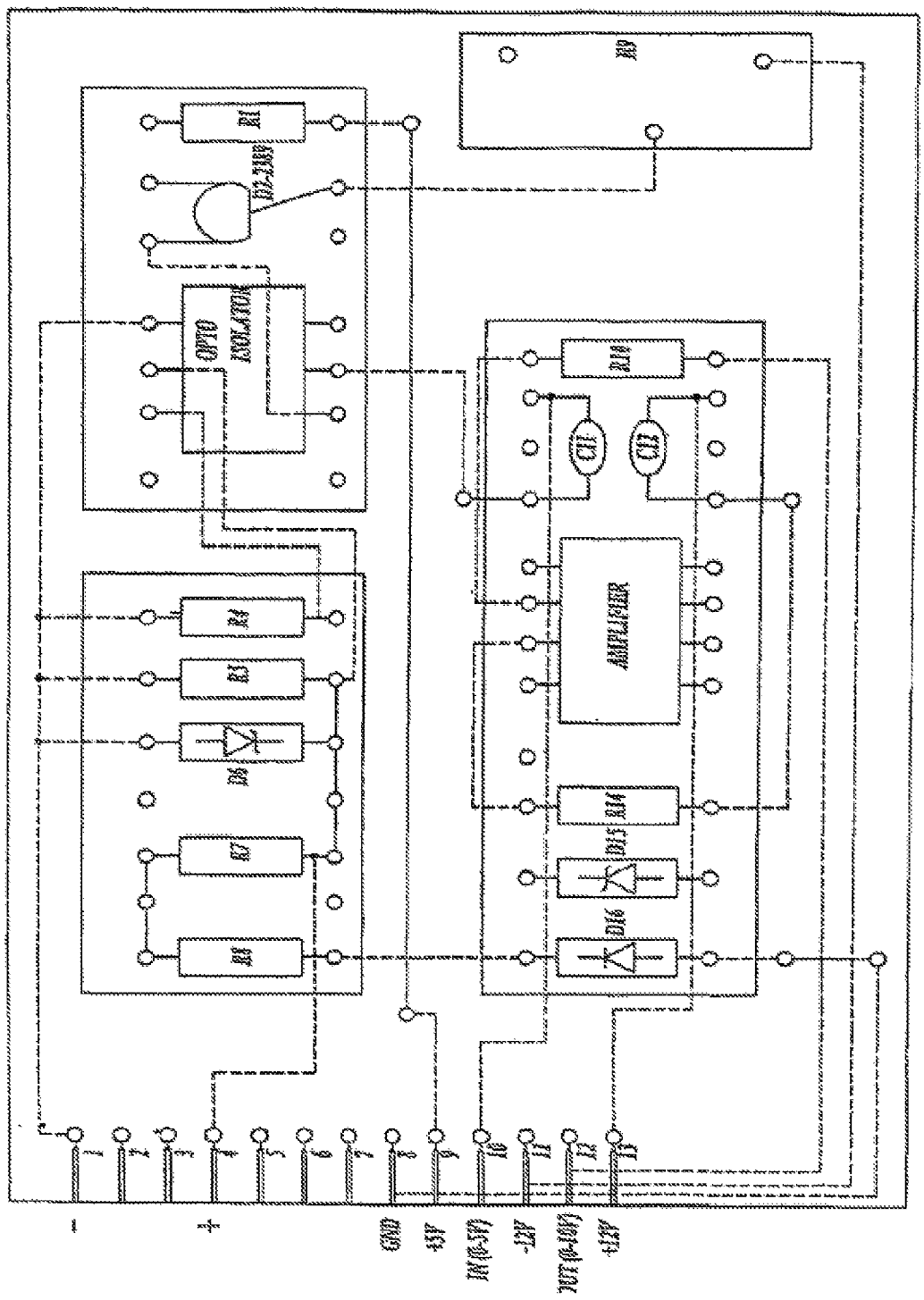
FIG. 14 is a circuit diagram of a representative controller unit.
Figure 15:
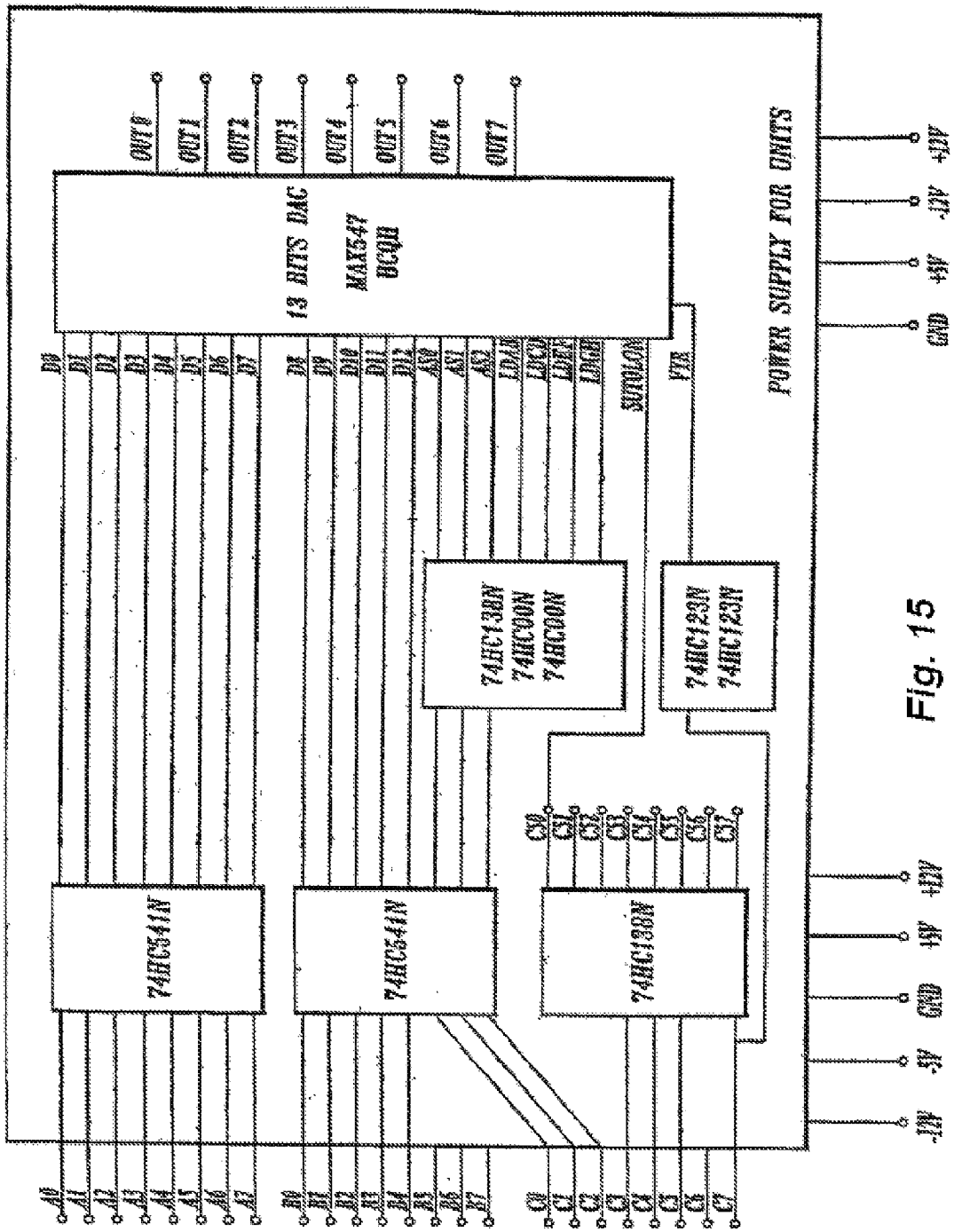
FIG. 15 is a schematic illustration of a representative DAC board circuit diagram illustrating connections.
Figure 16A:
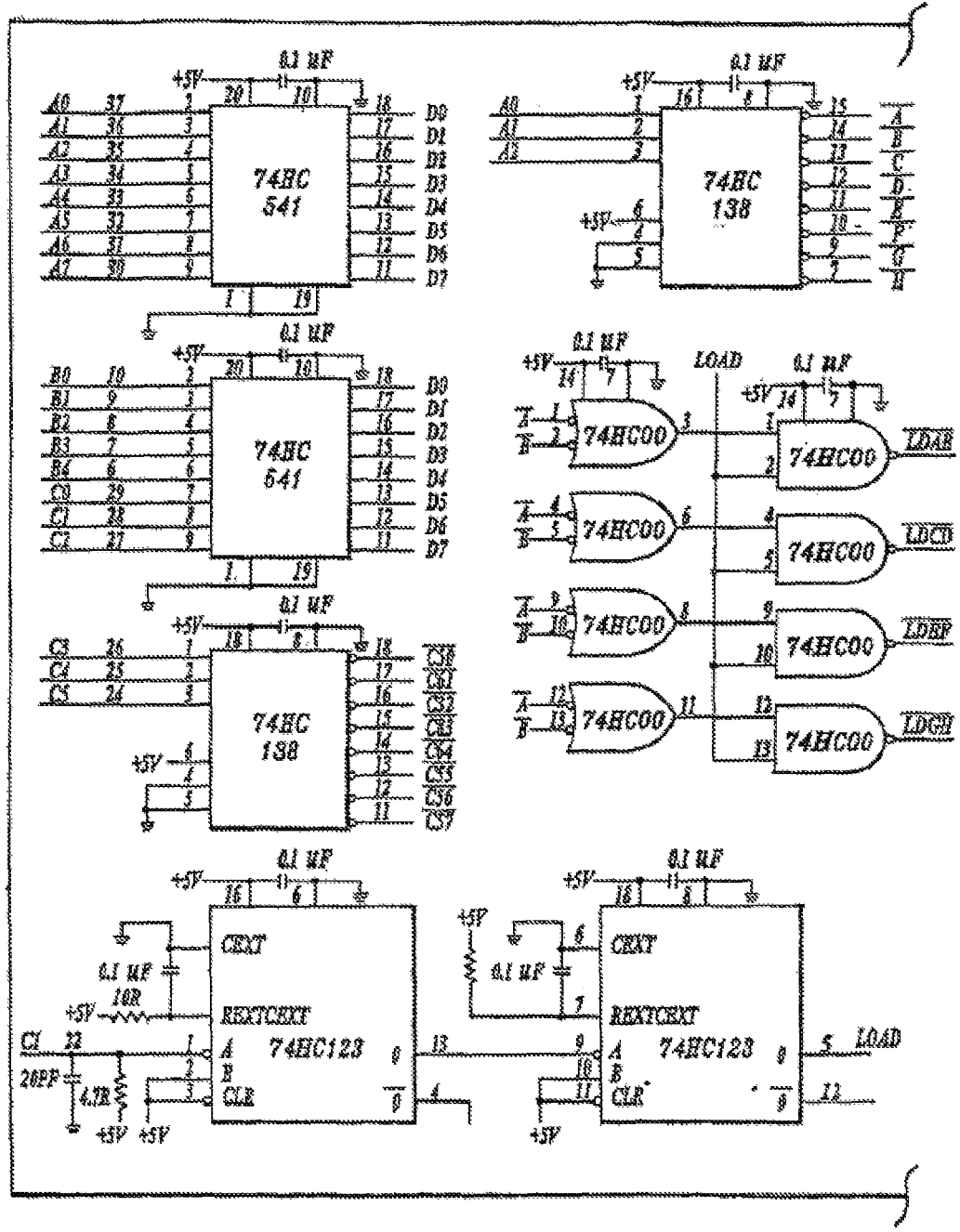
FIGS. 16A and 16B are schematic illustrations of representative DAC board circuit diagrams illustrating components of certain exemplary embodiments of the devices disclosed here.
Figure 16B:
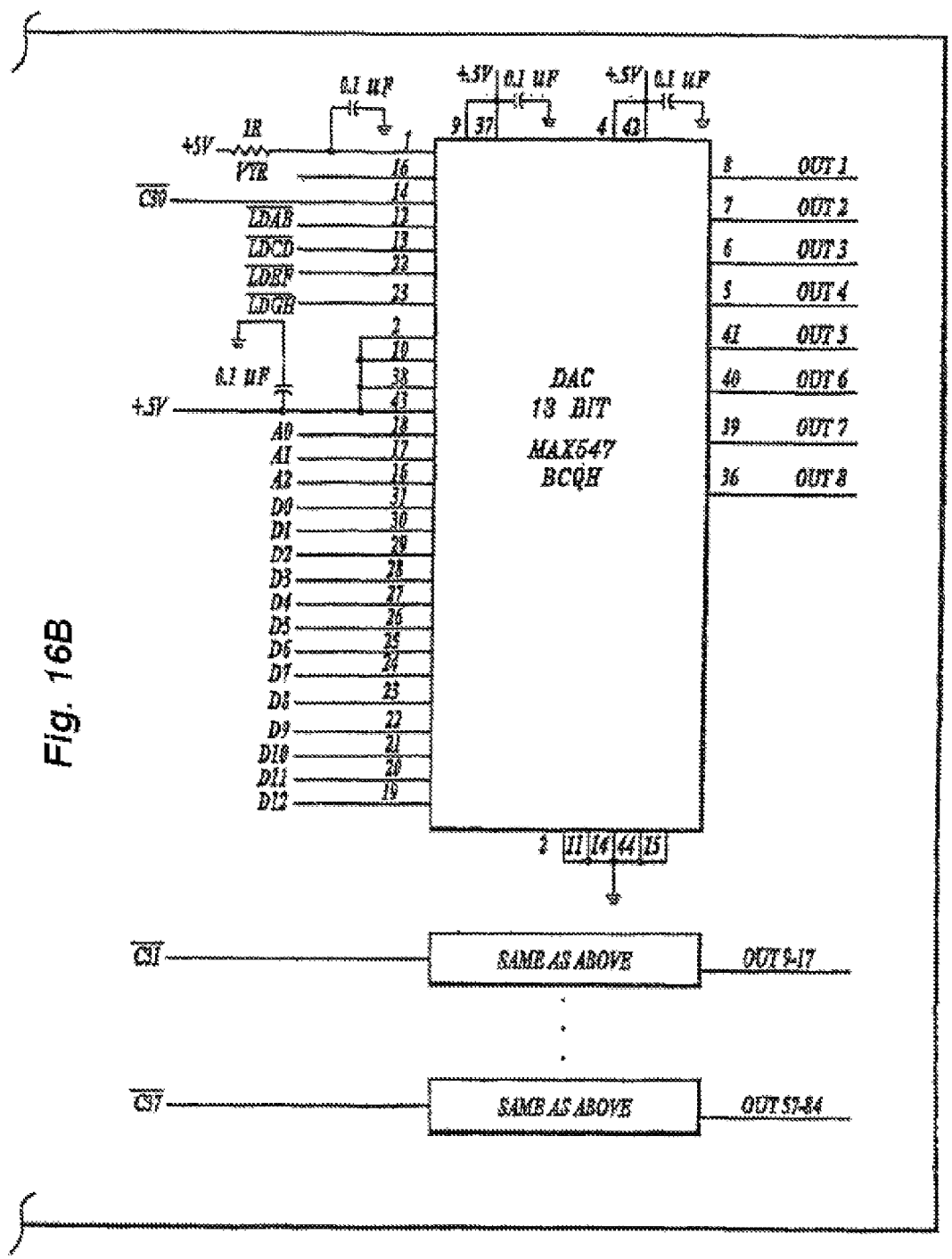

The gradient control is accomplished with PC-controlled circuits, diagrammed in FIG. 13, which are composed of electronic circuit boards. Pin 1 and 4 are connected to electrodes and neighboring units. The electrical potential on the electrode is reduced by 1/100, then enters amplifier LF411C where the load of the signal is increased. The signal is then sent to EXP32 board through pin 12, and the control signal (pin 10, 0-5 V) from the DAC board adjusts the current going through the optical isolator MCT275. A circuit diagram of the controller unit is shown in FIG. 14. A logic diagram for circuit diagram for ADC board is shown in FIG. 15. A circuit diagram for the ADC board with components identified is shown in FIGS. 16A and B.

The circuits scan all 50 electrodes and scale the signals down by 1/100. Then the signals are sent to ADC board where 0-10V analog signals are digitized. The computer compares these readings with the programmed gradient, then sends its commands in digital signals to DAC board via the Digital I/O boards. In the DAC board, the command signals are converted to 0-5V analog signals, then sent to the 50 units on the PC monitor/controller board. Those units adjust the current going through the units or changes the values of resistance Rxi. Note that the Rxi do not exist physically, and they are the resistance to current going through the chip MCT275, an optically isolated controller. The scan/response cycle for the circuits is set at about 0.5 sec, and could be adjusted by the program.

In some examples a suitable power supply, such as a 600V DC power supply (Xantrex), supplies power to the bulk fluid flow gate. The power to all the boards is typically supplied by the computer's power supply.

Figure 17A:
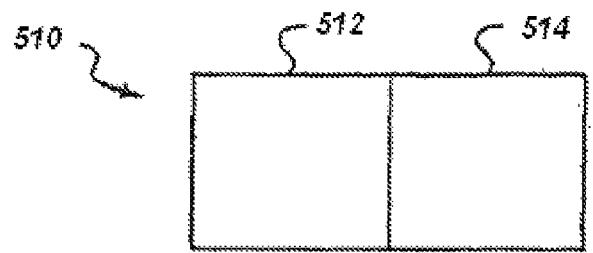
FIGS. 17A-C are schematic illustrations of representative configurations for other examples of the devices disclosed here.
Figure 17B:
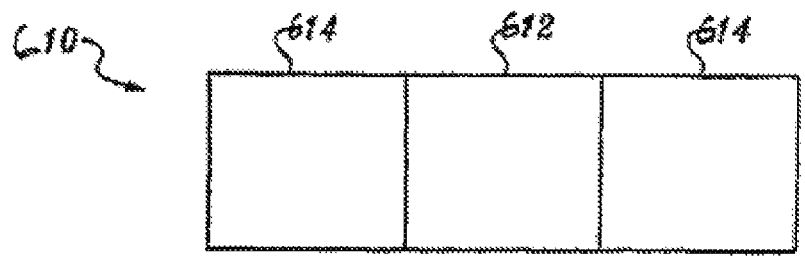
Figure 17C:
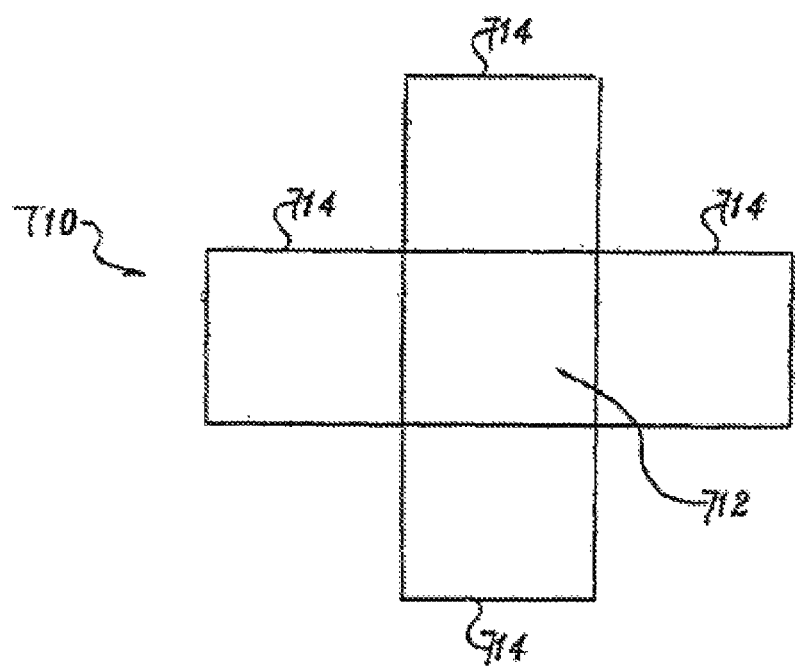

As noted above, the electrode housings can include more than one electrode array. For example, two electrode arrays can be associated with the first chamber in a configuration in which the first chamber is positioned in between the two arrays. Similarly, the first chamber can include, for example, four electrode arrays positioned about the first chamber in a quadrupole-type configuration. Representative devices including one, two, and four electrode arrays are illustrated schematically in FIGS. 17A-C. Representative device 510 including a single electrode array (i.e., located in electrode housing 514) and a first chamber (i.e., chamber 512) is shown in FIG. 17A. FIGS. 17B and 17C illustrate representative devices 610 and 710 having two and four electrode arrays and electrode chambers 614 and 714 arranged about separation chamber 612 and 712, respectively.

In accordance with certain examples, solvents that are used in the devices and methods disclosed here can be degassed prior to introduction into the bulk fluid flow gate. Without wishing to be bound by any particular scientific theory, it is believed that dissolved gases in the fluids can affect the reproducibility of the flow rates of the fluids. To achieve constant and reproducible flow rates, it may be necessary to remove at least some of the dissolved gases from any solvents prior to introduction of the solvents into the devices described here. The person of ordinary skill in the art, given the benefit of this disclosure, will be able to select suitable techniques for degassing the solvents including, but not limited to, vacuum filtration of the solvents, e.g., filtration through a fritted funnel, bubbling of inert gases, such as, for example, argon and nitrogen, through the solvents, and the like.

In accordance with some examples, a solvent gradient can be used such that the composition of the bulk fluid is altered during migration of the analytes in the sample. As used here, solvent gradient refers to variation in the composition of the bulk fluid during migration of analyte and/or separation of the analytes. For example, in a separation using bulk fluid comprising two solvents, A and B, the separation may begin with 100% solvent A as bulk fluid. As the separation progresses, the amount of solvent B can be increased, e.g., linearly, stepwise, logarithmically, etc., such that the composition of the bulk fluid introduced into the first chamber includes both A and B. Typically, the amount of each solvent in the solvent gradient is controlled by varying the amount of solvent introduced into the first chamber. In certain examples, it may be necessary to provide a mixing chamber so that the solvent can be mixed prior to introduction of the solvents into the devices described here. In other examples, the solvent gradients are computer controlled to provide high precision for the separations. One skilled in the art, given the benefit of this disclosure, will be able to select suitable solvent gradients for use in the devices and methods disclosed here.

In accordance with certain examples, lipids may be introduced either in the bulk fluid or in the loaded sample. Without wishing to be bound by any particular scientific theory, lipids typically are either hydrophobic, having only nonpolar groups, or can be amphipathic, having both polar and nonpolar groups. In embodiments where one or more analytes is uncharged, it may be necessary to introduce an amphipathic lipid into the sample. Again without wishing to be bound by any particular scientific theory, the nonpolar group of the lipid can associate with one or more uncharged analytes, e.g., through hydrophobic interactions, hydrogen bonding, dipolar interactions, and the like, while the polar group of the lipid remains free to provide an overall charge to the lipid-analyte complex. In certain embodiments, lipids are selected from phosphatidic acid, phospholipids and glycerophospholipids such as, for example, phosphatidylcholine, phosphatidylethanolamine, phosphatidylserine, cardiolipin, phosphatidylglycerol, phosphatidylinositol, and the like. In other embodiments, the lipids may include ether glycerophospholipids, cerebrosides, sphingolipids, and the like. One skilled in the art, given the benefit of this disclosure, will be able to select suitable lipids for use in the devices and methods disclosed here.

In accordance with other examples, the lipids can form micelles that may associate with one or more analytes. Without wishing to be bound by any particular scientific theory, because the amphipathic lipids typically include a nonpolar group and a polar group, when the lipids are placed into an aqueous solvent, the lipids typically spontaneously associate with each other such that the polar groups are positioned outward towards the aqueous solvent and the nonpolar groups are positioned inward away from the aqueous solvent. Typically, it is necessary to provide the lipids in a sufficient amount, e.g. a critical micelle concentration (CMC), such that micelles can spontaneously form. That is, when the lipids are present at concentration below the CMC, the predominant form is individual free lipids. When the lipids are present at a concentration greater than or equal to the CMC, the predominant form is micelles. Suitable CMC concentrations will be readily selected by those skilled in the art, given the benefit of this disclosure, and the CMC concentration typically depends on the type of lipid selected.

In accordance with some examples, the lipids may form vesicles, e.g., unilamellar (large unilamellar vesicles (LUVs), small unilamellar vesicles (SUVs)) or multilamellar vesicles. Such vesicles are typically characterized as including one or more bilayers formed when the nonpolar groups of the lipids associate with each other. Suitable methods for preparing vesicles will be readily selected by those skilled in the art, given the benefit of this disclosure, and include but are not limited to extrusion, sonication/extrusion, and the like.

In accordance with certain examples, when the device of FIG. 2a is used to purify a sample or separate analytes in a sample, sample is introduced into first chamber 17 through second entry port 21. Bulk fluid flows substantially downward towards first exit port 23. The charge of the electrodes is selected such that at least some of the analytes in the sample will migrate upstream towards second exit port 25. The velocity and volume of bulk fluid is selected such that the analyte migrates with a suitable migration rate. In examples employing a substantially constant electric field, the velocity and/or volume of bulk fluid introduced into first chamber 17 can be increased such that hydrodynamic resistance is substantially greater than the driving force provided by the electric field. In such cases, substantially all of the analyte will migrate towards first exit port 23. Depending on the selected strength of the electric field and the selected hydrodynamic force from bulk fluid, the migration rate and migration direction of analyte may be controlled.

In the device shown in FIG. 2a, because bulk fluid flows substantially downstream towards first exit port 23, hydrodynamic resistance at first exit port 23 is substantially greater than hydrodynamic resistance at second exit port 25. A result of such differential hydrodynamic resistance is that once the analyte migrates upstream of first entry port 20, the rate of migration depends more on the electric field strength and less on the flow of bulk fluid. At points proximate to first entry port 20, a gating effect is observed as analytes approach the portion of first chamber 17 near first entry port 20. Once the analyte clears the first entry port, e.g., once the analyte migrates upstream of first entry port 20, the gating effect of bulk fluid becomes minimal, or in certain examples, the gating effect is non-existent.

In certain examples and referring to FIG. 19a, during operation of the bulk fluid flow gate, sample 600 is introduced into the first chamber 200 through second entry port 2c. In this example, the sample comprises a single charged analyte that is negatively charged. In the presence of an electric field, the sample will be driven towards positively charged electrode 300a and away from negatively charged electrode 300b.

In certain examples, the hydrodynamic force generated by bulk fluid and the driving force generated by the electric field are selected such that the sample is allowed to migrate towards second exit port 2a. Without wishing to be bound by any particular scientific theory, the operating parameters in this example are selected such that upon arrival of the analyte at first entry port 2b, the hydrodynamic force and the driving force of the electric field are approximately equal so that no net migration of analyte 600*a* occurs (see FIG. 19*b*). Impurities in the sample are allowed to migrate and exit the first chamber either through first exit port 2*d* or second exit port 2*a*. After exiting of impurities, the analyte can exit through the second exit port by increasing the electric field strength and/or reducing the hydrodynamic force generated by bulk fluid flow. In examples where it is desirable to exit the analyte from the first exit port, the hydrodynamic force can be increased or the electric field strength can be decreased so that the sample exits from the first exit port. It will be within the ability of the person of ordinary skill in the art to select suitable hydrodynamic forces and electric field strengths so that the analyte will exit from either the first exit port of the second exit port.

In other examples and referring to FIG. 20*a*, during operation of the bulk fluid flow gate, sample 600 is introduced through second entry port 2*c*. In the example shown in FIGS. 20*a* and 20*b*, the sample comprises two analytes—one positively charged and one negatively charged. Bulk fluid 5 is flowed into chamber 200 through first entry port 2*b* and exits chamber 200 though first exit port 2*d*, which is downstream of first entry port 2*b* and second entry port 2*c*. The analytes typically will migrate towards the electrode having an opposite charge. One analyte of the sample will migrate towards electrode 300*a* and the other analyte of the sample will migrate towards electrode 300*b*. Without wishing to be bound by any particular scientific theory, because analyte 600*b* migrates in the same direction as bulk fluid flow, analyte 600*b* typically will exit the first chamber, through first exit port 2*d*, faster than analyte 600*a* will exit the first chamber. In particular, the driving force of the electric field should exceed the hydrodynamic force generated by bulk fluid flow for analyte 600*a* so that the analyte can migrate towards second exit port 2*a*. Depending on the selected hydrodynamic force and selected electric field strength, the migrating analyte can be halted at any portion in the chamber. In certain examples, the hydrodynamic force and electric field strength are selected such that once analyte 600*a* migrates to a position proximate first entry port 2*b*, the analyte is held in this position until a user desires to elute the analyte from the chamber through second exit port 2*a*. In certain examples, the analyte is held proximate to first entry port 2*b* until substantially all other analyte exits the chamber through first exit port 2*a* (see FIG. 19*c*). Then, in certain examples, the hydrodynamic force is increased, or the electric field strength is decreased, and analyte 600*a* is pushed back downstream of the first entry port and exits through first exit port 2*d*. In other examples, the hydrodynamic force is decreased and/or the electric field strength is increased and analyte 600*a* exits the first chamber through second exit port 2*a*. It will be within the ability of the person of ordinary skill in the art to select suitable hydrodynamic forces and electric field strengths to elute analytes from a desired port.

In certain exemplary embodiments, a system is provided comprising a fluid logic device as disclosed here, including one or more of the above described bulk fluid flow gates. The bulk fluid flow gates of such exemplary systems typically each includes at least one electrode for generating an electric field, e.g., an electrode pair or an electrode array, a first chamber in communication with the at least one electrode, the first chamber comprising an first entry port, a first exit port, a second entry port positioned between the first entry port and the first exit port, and a second exit port. The system also typically includes a sample loader such as an injector in communication with the second entry port of the first chamber. The injector provides for the ability to load samples into the system. Suitable injectors will be readily apparent to those skilled in the art, given the benefit of this disclosure and exemplary injectors include loop-injectors, automated liquid handlers, auto-samplers, direct syringe feed and the like. The system also includes one or more detectors for detecting analytes as the analytes exit the first chamber. It is possible to configure the system with innumerable types of detectors. Exemplary detector include UV/Visible detectors, nuclear magnetic resonance detectors, infrared detectors, fluorescence detectors, electrochemical detectors, and mass spectrometers. Typically the detectors include a flow cell such that analyte exits the first chamber, through either the first or second exit port, and flows into the flow cell of the detector where it is detected. It will be within the ability of those skilled in the art, given the benefit of this disclosure, to select and design suitable systems for separating and detecting one or more analytes in a sample.

In certain examples it may be necessary to degas the bulk fluid to remove any dissolved gases in the bulk fluid to minimize pressure fluctuations in the chamber or to reduce the likelihood of variations in flow rate. Suitable degassing techniques are known to the person of skill in the art and include but are not limited to bubbling of inert gases, such as, for example, nitrogen or argon, through the solvents, filtration of the solvents through a microporous filter, and the like.

In certain examples, flow rate of the bulk fluid is altered or changed during migration of the charged analytes. For example, the flow rate of bulk fluid can be altered throughout the focusing or separation to increase the opposing force, i.e., the hydrodynamic force, against the migrating sample or decrease the opposing force against the migrating sample. In some examples, the flow rate is controlled by a microprocessor such that reproducible flow rates can be used for subsequent separations.

In accordance with certain examples, a given set of focusing process parameters, as noted above, includes all parameters, both dynamic and non-dynamic, that affect the location of an analyte in the first chamber. Such factors include but are not limited to, for example, dynamic factors, or factors that are capable of being changed, such as the particular characteristics such as the shape and strength of the electric field gradient; the composition, concentration and pH of bulk fluid; the flow rate of bulk fluid; the composition, concentration and pH of the coolant fluid flowing through the electrode housing; the flow rate of the coolant; and other such dynamic factors. The parameters that make up the process parameters further include non-dynamic factors such as the dimensions of the first chamber and second chamber, and other such non-dynamic factors.

In some examples, in simultaneous separation in a first chamber of multiple charged analytes having the same or similar charge to mass ratios, the velocity of the bulk fluid and the electric field strength are each chosen such that the location of the stationary focused band of each such analyte is shifted in the chamber to a different degree and preferably there is "baseline" separation between the different analytes such that each analyte may be removed from the chamber substantially free from contamination by other analytes. It should be understood, however, that reference here to each of multiple analytes being shifted to a different degree does not exclude the possibility that in any given stationary focused band there may be more than one analyte, that is, there may be analyte mixtures for which the devices and methods disclosed here are operative to establish focused bands of subsets of the analytes, each subset containing one or more of the analytes.

In certain examples, the bulk fluid may comprise water, a suitable buffer, organic solvents, ion-pairs and the like. Generally, high concentrations of buffer are used to stabilize samples comprising biomolecules, such as proteins, for example. However, as ionic strength of the buffer increases, so does the conductivity of the buffer. Such increases in conductivity can increases the heat generation and power consumption and can set a limit for the highest suitable field strength. Typical field strengths include, for example, 180 to 300 V/cm. In some examples, the same solution is used as bulk fluid and as the solvent which the sample is dissolved in. The fluid in a direction substantially opposite bulk fluid flow and, in certain examples, flows upward in the electrode housing such that any gas bubbles generated at the electrodes are removed from the electrode housing. In addition, the fluid in the electrode housing acts as coolant to remove the heat generated. In certain examples, the fluid of the electrode housing is circulated through a cooling apparatus, such as a cooling bath, heat exchanger, and the like, to remove the heat from the fluid, and the may then be recycled back into the electrode housing.

In certain examples, molecular sieves, other separation media, may be included in the first chamber. The molecular sieves include any medium or substance, for example suitable organic or inorganic polymer or the like, by which shifting of the focusing location is achieved. The molecular sieve is selected for its ability to shift the location of the stationary focused band of analyte for simultaneous focusing of multiple charged analytes. Preferably, a molecular sieve is chosen such that the amount to which the stationary focused bands of analyte are shifted for a given set of focusing conditions varies with the size or molecular weight of the analyte. Preferably the degree of shift varies proportionally with the molecular weight of the analyte, for example, such that each stationary focused band of charged analyte is focused at a stable location separate from the other charged analytes. Factors that affect the selection of a particular molecular sieve at a particular concentration include, for example, the size of the molecules to be separated and focused, the pH at which the system is operated, and other such relevant factors that will be apparent to those skilled in the art, given the benefit of this disclosure. In certain examples, the molecular sieve comprises a gel, which may be either an organic gel or an inorganic gel or a combination of organic and inorganic gel. The gel may be a fixed gel. A fixed gel optionally may be polymerized within the first chamber, such that it does not substantially flow or move when bulk fluid is flowed through the first chamber. Alternatively, the gel may be a soluble gel that is dissolved in the bulk fluid, such that the gel flows with the bulk fluid when the bulk fluid liquid flows through the first chamber. In certain examples, the soluble gel is introduced into the chamber and resides there during focusing. As used herein, the term "soluble gel" refers to a gel that is soluble or dissolved in a liquid or fluid, and further refers to gels that form suspensions, emulsions, colloids, and the like. Typically, soluble gels comprise polymers having little or no cross-linking. In certain examples, the gel will be comprised of molecules having a molecular weight of between about 2000 and about 100,000 Daltons. Suitable gels include, for example, linear polyacrylamide, polyvinyl alcohol, methyl cellulose and other derivatized celluloses, and the like. Other suitable molecular sieves include microporous structures composed of either crystalline aluminosilicate, chemically similar to clays and feldspars and belonging to a class of materials known as zeolites, or crystalline aluminophosphates derived from mixtures containing an organic amine or quaternary ammonium salt, or crystalline silicoaluminophosphates which are made by hydrothermal crystallization from a reaction mixture comprising reactive sources of silica, alumina and phosphate, and the like. The person of ordinary skill in the art, given the benefit of this disclosure, will be able to select suitable gels and sieves through routine experimentation, utilizing known methods, for example by the methods described in Ackers et al., "Determination of stoichiometry and equilibrium constants for reversibly associating systems by molecular sieve chromatography," *Proc. Nat. Acad. Sci. USA* 53: 342-349 (1965), the entire disclosure of which is hereby incorporated by reference in its entirety for all purposes. Other suitable sieves will be readily apparent to those of ordinary skill in the art, given the benefit of the present disclosure.

In accordance with other examples, all fluid used in operation of the bulk fluid gate comprise buffer. Generally, a higher concentration of buffer stabilizes the protein sample and avoids precipitation. However, as discussed above, high ionic strength means high conductivity of the buffer, which increases the heat generation and power consumption and sets a limit for the highest suitable field strength. Typical field strengths include, for example, 180 to 300 v/cm. Advantageously, the same buffer is used for the first liquid and second liquid, excluding the dissolved gel where a soluble gel is used to ensure the ion balance between the two sides. The buffer in the second chamber goes upward in the electrode chamber, effectively removing the tiny gas bubbles generated at the electrodes and acts as coolant to remove the Joule heat generated. In certain examples, this coolant is then run through a cooling apparatus, such as a cooling bath, heat exchanger, and the like, to remove the heat from the coolant and the coolant is then recycled back into the electrode housing.

Another role of the coolant is to conduct the electric field gradient through the permeable membrane to the first chamber. Suitable bulk fluids and coolants will be readily apparent to those of ordinary skill in the art, given the benefit of this disclosure.

In accordance with an example of a method, an electrophoretic method for focusing a charged analyte is provided. In the method, a device in accordance with the examples above is provided, a first fluid comprising at least one charged analyte is introduced into the first chamber and an electric field gradient, in the presence of bulk fluid flow, is applied to the charged analyte in the first chamber to focus the charged analyte in the electric field gradient, wherein the first chamber optionally contains chromatography media such as, for example, molecular sieve operative to shift the location at which a stationary focused band of a charged analyte forms under a given set of focusing process parameters. The electric field gradient is preferably generated by an electrode array by individually adjusting the electrode voltages of each element of the array. In certain examples, the electric field gradient is dynamically controlled, that is to say the electric field gradient is changed or adjusted while the focusing takes place.

In certain exemplary embodiments, a hydrodynamic force is generated by pumping the first fluid through the first chamber. The bulk fluid typically is a liquid with any suitable flow rate. In accordance with certain exemplary embodiments the flow rates are as follows. In micro-scale embodiments of the devises and methods disclosed here, exemplary flow rates are 0-20 microliters per minute. In micro-bore scale embodiments of the devises and methods disclosed here, exemplary flow rates are 20-100 microliters per minute. In analytical scale embodiments of the devises and methods disclosed here, exemplary flow rates are 1.0 mL/min. to 2.0 mL/min. In preparative scale embodiments of the devises and methods disclosed here, exemplary flow rates are 2.0 to 20.0 mL/min. In process scale embodiments of the devises and methods disclosed here, exemplary flow rates are 20 mL/min and higher. The flow rate is chosen to provide the desired separation, in other words so that the hydrodynamic force counters the electric field gradient at a position between the weakest and the strongest part of the electric field. In this fashion, the analyte will be retained within the first chamber. Factors that affect the choice of flow rate include, for example, the viscosity and density of the liquid, strength of the electric field gradient, net charge of the analyte, etc. Suitable flow rates will depend in part upon the electric field gradient that is chosen. Suitable flow rates can be readily selected by those skilled in the art, given the benefit of this disclosure.

Certain examples of the devices and methods herein are suited for focusing and separating charged analytes. Charged analytes that can be focused include, e.g., charged polymers, carbohydrates, and biological analytes, such as proteins, peptides, oligonucleotides, polynucleotides, hormones, biomarkers, and the like, and mixtures of any of these. In particular, charged analytes which have similar charge to mass ratios, such as DNA, RNA, etc., can be separated and focused on the basis of differences in their respective molecular weights.

In accordance with certain examples, analytes with little or no net charge can be complexed with to charged carriers, for example, as discussed above, micelles and liposomes, can also be focused and separated with the device. For example, proteins that exhibit little net charge can form a complex with a charged carrier such that the protein acquires the charge of the charged carrier. In certain examples, a detergent, for example sodium dodecyl sulfate (SDS), is used as the charged carrier. Without wishing to be bound to a theory, it is presently believed that the SDS binds strongly to protein molecules and "unfolds" them into semi-rigid rods whose lengths are proportional to the length of the polypeptide chain, and hence approximately proportional to molecular weight. Because of the magnitude of the charge of the bound detergent molecules, the protein complexed with such a detergent takes on a high net charge.

In certain examples, electrophoretic devices and methods are provided for focusing a charged analyte and for simultaneously focusing and separating multiple charged analytes. The device comprises a first chamber, as discussed above; an electrode housing that includes an inlet for introducing a second liquid into the electrode housing and an outlet for exiting the second liquid from the electrode housing; and permeable material separating the first and second chambers. The method of separating charged analytes comprises introducing a first fluid comprising a plurality of charged analytes into the bulk fluid flow gate, flowing bulk fluid into the first chamber and applying an electric field gradient to the charged analyte to focus the charged analyte in the electric field gradient into stationary focused bands of charged analyte. In this example, it will be understood that the focusing and separation of these devices and methods occur simultaneously.

What is claimed is:

1. A fluid logic device comprising:
a first flow channel;
a first bulk fluid flow gate in fluid communication with the first flow channel;
a second bulk fluid flow gate in communication with the first bulk fluid flow gate;
a third bulk fluid flow gate in fluid communication with the first bulk fluid flow gate, the first bulk fluid flow gate, the second bulk fluid flow gate, and the third bulk fluid flow gate each comprising
a first entry port for introducing bulk fluid into a first chamber,
a first exit port for exiting of bulk fluid from the first chamber,
a second entry port positioned between the first entry port and the first exit port, the second entry port for introducing sample into the first chamber, and
a second exit port, in which bulk fluid introduced through the first entry port experiences substantially greater hydrodynamic resistance at the first exit port than at the second exit port;
the first exit port of the first bulk fluid flow gate being in fluid communication with the second entry port of the third bulk fluid flow gate; and
means for generating an electric field in electrical communication with the first bulk fluid flow gate and means for generating an electric field in electrical communication with the second bulk fluid flow gate.

* * * * *